(12) United States Patent
Bevernage et al.

(10) Patent No.: US 12,145,933 B2
(45) Date of Patent: Nov. 19, 2024

(54) HEMI (L)-TARTRATE FORMS OF 3-({5-CHLORO-1-[3-(METHYLSULFONYL) PROPYL]-1H-INDOL-2-YL}METHYL)-1-(2,2,2-TRIFLUOROETHY)-1,3-DIHYDRO-2H-IMIDAZO[4,5-C]PYRIDIN-2-ONE AND PHARMACEUTICAL COMPOSITIONS COMPRISING THE SAME

(71) Applicant: Janssen Sciences Ireland Unlimited Company, County Cork (IE)

(72) Inventors: Jan Jos L. Bevernage, Kuringen (BE); Jasmine Bogaerts, Mol (BE); Kristof Leonard Kimpe, Beerse (BE); Eszter Tieger, Magyarlak (HU)

(73) Assignee: Janssen Sciences Ireland Unlimited Company, County Cork (IE)

( * ) Notice: Subject to any disclaimer, the term of this patent is extended or adjusted under 35 U.S.C. 154(b) by 413 days.

(21) Appl. No.: 17/344,361

(22) Filed: Jun. 10, 2021

(65) Prior Publication Data

US 2021/0387984 A1 Dec. 16, 2021

(30) Foreign Application Priority Data

Jun. 11, 2020 (EP) .................................. 20179407

(51) Int. Cl.
| | |
|---|---|
| *C07D 471/04* | (2006.01) |
| *A61K 9/00* | (2006.01) |
| *A61K 47/02* | (2006.01) |
| *A61K 47/26* | (2006.01) |
| *A61K 47/38* | (2006.01) |

(52) U.S. Cl.
CPC .......... *C07D 471/04* (2013.01); *A61K 9/0095* (2013.01); *A61K 47/02* (2013.01); *A61K 47/26* (2013.01); *A61K 47/38* (2013.01); *C07B 2200/13* (2013.01)

(58) Field of Classification Search
CPC ....... C07D 471/04; A61K 47/02; A61K 47/26
USPC ......................................................... 514/303
See application file for complete search history.

(56) References Cited

U.S. PATENT DOCUMENTS

| | | |
|---|---|---|
| 6,489,338 B2 | 12/2002 | Yu et al. |
| 6,506,738 B1 | 1/2003 | Yu et al. |
| 6,534,535 B1 | 3/2003 | Zhu et al. |
| 6,919,331 B2 | 7/2005 | Yu et al. |
| 7,361,657 B2 | 4/2008 | Janssens et al. |
| 7,528,149 B2 | 5/2009 | Janssens et al. |
| 8,846,672 B2 | 9/2014 | Cooymans et al. |
| 8,865,705 B2 | 10/2014 | Cooymans et al. |
| 8,921,560 B2 | 12/2014 | Cooymans et al. |
| 8,927,720 B2 | 1/2015 | Cooymans et al. |
| 9,051,317 B2 | 6/2015 | Cooymans et al. |
| 9,321,767 B2 | 4/2016 | Cooymans et al. |
| 9,321,768 B2 | 4/2016 | Cooymans et al. |
| 9,339,494 B2 | 5/2016 | Cooymans et al. |
| 2002/0016309 A1 | 2/2002 | Yu et al. |
| 2004/0166137 A1 | 8/2004 | Lackey |
| 2011/0009444 A1 | 1/2011 | Dubois et al. |
| 2013/0261151 A1 | 10/2013 | Cooymans et al. |
| 2013/0267508 A1 | 10/2013 | Cooymans et al. |
| 2013/0267555 A1 | 10/2013 | Cooymans et al. |
| 2013/0267556 A1 | 10/2013 | Cooymans et al. |
| 2013/0324527 A1 | 12/2013 | Cooymans et al. |
| 2015/0073012 A1 | 3/2015 | Cooymans et al. |
| 2015/0073013 A1 | 3/2015 | Cooymans et al. |
| 2015/0111868 A1 | 4/2015 | Tahri et al. |
| 2015/0158862 A1 | 6/2015 | Tahri et al. |
| 2015/0166533 A1 | 6/2015 | Tahri et al. |
| 2015/0175608 A1 | 6/2015 | Tahri et al. |
| 2015/0231119 A1 | 8/2015 | Cooymans et al. |
| 2015/0259367 A1 | 9/2015 | Tahri et al. |
| 2016/0122346 A1 | 5/2016 | Tahri et al. |
| 2016/0237083 A1 | 8/2016 | Cooymans et al. |
| 2016/0237096 A1 | 8/2016 | Cooymans et al. |
| 2016/0251377 A1 | 9/2016 | Cooymans et al. |

FOREIGN PATENT DOCUMENTS

| | | |
|---|---|---|
| FR | 2926556 | 7/2009 |
| JP | 2008522968 | 6/2006 |
| WO | 199801428 A1 | 1/1998 |
| WO | 2000020400 A1 | 4/2000 |
| WO | 2000035886 A2 | 6/2000 |
| WO | 2001057019 A1 | 8/2001 |
| WO | 2001057020 | 8/2001 |
| WO | 2001/95910 A1 | 12/2001 |
| WO | 2002026228 A1 | 4/2002 |
| WO | 2003049688 A2 | 6/2003 |
| WO | 2003/056344 A2 | 7/2003 |
| WO | 2003053344 A2 | 7/2003 |
| WO | 2004/069256 A1 | 8/2004 |
| WO | 2006062465 A1 | 6/2006 |
| WO | 2006062565 A1 | 6/2006 |
| WO | 2008/147697 A1 | 12/2008 |
| WO | 2012/080447 | 6/2012 |
| WO | 2012/080449 A1 | 6/2012 |

(Continued)

OTHER PUBLICATIONS

Vendeville et al., Journal of Medicinal Chemistry, (2020), 63(15), pp. 8046-8058.*

(Continued)

*Primary Examiner* — Niloofar Rahmani

(57) ABSTRACT

The present invention relates to hemi (L)-tartrate forms of the RSV fusion inhibitor 3-({5-chloro-1-[3-(methylsulfonyl) propyl]-1H-indol-2-yl}methyl)-1-(2,2,2-trifluoroethyl)-1,3-dihydro-2H-imidazo[4,5-c]pyridin-2-one (also known under its INN as rilematovir), and to processes for preparing said forms and the use of these forms in a pharmaceutical composition.

19 Claims, 7 Drawing Sheets

(56) References Cited

FOREIGN PATENT DOCUMENTS

| WO | 2012/080450 A1 | 6/2012 |
|---|---|---|
| WO | 2012080446 A1 | 6/2012 |
| WO | 2012080451 A1 | 6/2012 |
| WO | 2012080481 A1 | 6/2012 |
| WO | 2013/186332 A1 | 12/2013 |
| WO | 2013/186333 A1 | 12/2013 |
| WO | 2013/186334 A1 | 12/2013 |
| WO | 2013/186335 A1 | 12/2013 |
| WO | 2019/110563 A1 | 6/2019 |

OTHER PUBLICATIONS

Banker, et al., "B. Prodrugs", Modern Pharmaceutics, 3rd Edition, pp. 451 and 596, (1996).
Beaulieu, et al., "Improved Replicon Cellular Activity of Non-Nucleoside Allosteric Inhibitors of HCV NS5B Polymerase: From Benzimidazoles to Indole Scaffolds", Bioorganic & Medicinal Chemistry Letters, vol. 16: pp. 4987-4993 (2006).
Eun Hee Lee, A practical guide to pharmaceutical polymorph screening & selection, Asian J. of Pharmaceutical sciences, Mar. 16, 2014, pp. 163-175, vol. 9, No. 4.
Giampieri, et al., "Antiviral Activity of Indole Derivatives", Antiviral Research, vol. 83: pp. 179-185 (2009).
Goodman, et al., "Desymmetrization of Dichloroazaheterocycles", Tetrahedron, vol. 55: pp. 15067-15070 (1999).
Goodman, et al., "Biotransformation of Drugs", The Pharmacological Basis of Therapeutics, 8th Ed., Chapter 1, pp. 13-20 (1992).
Greene, et al., "Protection for The Hydroxyl Group Including 1,2- and 1,3-diols" Protective Groups in Organic Synthesis, 3rd edition, pp. 119-121 (1999). XP002670712.
Hallack, et al., "Glycosaminoglycan Sulfation Requirements for Respiratory Syncytial Virus Infection," Journal of Virology, vol. 74(22):pp. 10508-10513 (Nov. 2000).
Ito, et al., "A Medium-Term Rat Liver Bioassay for Rapid in vivo Detection of Carinogenic Potential of Chemicals", Cancer Science, vol. 94 (1): pp. 3-8 (Jan. 2003).
Mackman, et al., "Discovery of an Oral Respiratory Syncytial Virus (RSV) Fusion Inhibitor (GS-5806) and Clinical Proof of Concept in a Human RSV Challenge Study", Journal of Medicinal Chemistry, vol. 58: pp. 1630-1643 (2015).
Negishi, "3 Fluorine as an Organic Compound", Flourine Chemistry Towards New Functionality, pp. 89-90 (Jun. 30, 1988).
Nozaki, et al., "Chapter 5: Structure-Activity Relationship and Drug Design", Medicinal Chemistry, pp. 98-99 (Jul. 1, 1995).
Pearce, et al., "E-Novo: An Automated Workflow for Efficient Structure-Based Lead Optimization", J. Chem. Inf. Model., vol. 49: pp. 1797-1809 (2009).
Provencal, et al., "Development of an Efficient and Scalable Process of Respiratory Syncytial Virus Inhibitor", Organic Process Research & Development, 2004, pp. 903-908, vol. 8.
Qidong, et al., Pharmaceutical Chemistry, Chemical Industry Press, Jan. 2004, pp. 32-34, 2004.
Scifinder, CAS Registry No. 931665-23-5, CAS Registry No. 931665-23-5, Chemical Library, CAS Registry No. 931665-23-5, Enamine.
Scifinder, CAS Registry No. 941045-14-3, CAS Registry No. 941045-14-3, Chemical Library, CAS Registry No. 941045-14-3, Enamine.
Silverman (Ed.), "Section 2.2 Lead Modification: Drug Design and Development" The Organic Chemistry of Drug Design, 2nd Edition pp. 29-32 (2004).
Tonelli, et al., Antiviral Activiey of Benzimidazole Derivatives I., Chemistry & Biodiversity, vol. 5(11):pp. 2386-2401 (2008).
Venkatesh, et al., "Role of the Development Scientist in Compound Lead to Selection and Optimization", Journal of Pharmaceutical Sciences, Feb. 2000, pp. 145-154, vol. 89 (2).
Wang, et al., "Respiratory syncytial virus fusion inhibitors. Part 5 : Optimization of benzimidazole substitution patterns towards derivatives with improved activity", Bioorganic & Medicinal Chemistry Letters, vol. 17 (16): pp. 4592-4598 (Jul. 17, 2007).
Wang, et al., "Synthesis and Evaluation of Benzothiazole-Based Analogues as Novel, Potent, and Selective Fatty Acid Amide Hydrolase Inhibitors", J. Med. Chem., vol. 52: pp. 170-180 (2009).
Wermuth (Editor), "The Latest Medicinal Chemistry : Chapter 13—Molecular Variations based on Isosteric Replacement", The Latest Medicinal Chemistry, 1998, pp. 235-271, vol. 1.
Wermuth (Editor), "The Practice of Medicial Chemistry", The Lastest Medicinal Chemistry, 1993, pp. 375-380, vol. 1.
Wermuth et al., Molecular Variations Based on Isosteric Replacements, Practice of Medicinal Chemistry, 2008, 290-342, 3rd edition.
Wermuth, et al, The Practice of Medicinal Chemistry, Designing Prodrugs and Bioprecursors I: Carrier Prodrugs, 1996, pp. 672-696, vol. 31, Academic Press Limited.
West, "Chapter 10 Solid Solutions", Solid State Chemistry and its Applications, John Wiley & Sons, pp. 33-36 (1984).
Wolff (ed.), "Some Consideration for Prodrug Design", Burger's Medicinal Chemistry and Drug Discovery, Fifth Ed., vol. I: pp. 975-977 (1997).
Wolff, et al., Burger's Medicinal Chemistry and Drug Discovery, -, 1994, pp. 975-977, 5th Edition, vol. 1.
Wyde, et al., "CL387626 exhibits marked and unusual antiviral activity against respiratory syncytial virus in tissue culture and in cotton rats", Antiviral Research, vol. 38: pp. 31-42 (1998).
Yamanaka (Editor), "Introduction to Fluorine Chemistry: The Role of Fluorine Chemistry in Cutty Edge Technology", Japan Society for the Promotion of Science, 2005, pp. 398-403.
Yu, et al., "Respiratory syncytial virus fusion inhibitors. Part 4: Optimization for oral bioavaiability", Bioorganic & Medicinal Chemistry Letters, vol. 17(4): pp. 895-901 (2007).
Yu, et al., "Respiratory syncytial virus inhibitors. Part 2: Benzimidazol-2-one derivatives", Bioorganic & Medicinal Chemistry Letters, vol. 14:pp. 1133-1137 (2004).
ClinicalTrials.gov Identifier: NCT04583280, A Study of Rilematovir in Infants and Children and Subsequently in Neonates Hospitalized With Acute Respiratory Tract Infection Due to Respiratory Syncytial Virus (RSV) (DAISY), Oct. 12, 2020, https://clinicaltrials.gov/ct2/show/NCT04583280.
EudraCT No. 2020-002023-11, A Phase 3, Randomized, Double-blind, Placebo-controlled Study to Evaluate the Efficacy and Safety of Rilematovir in Infants and Children (≥28 Days to ≤5 Years of Age) and Subsequently in Neonates (28 Days of Age), Hospitalized With Acute Respiratory Tract Infection . . . , Nov. 3, 2020, https://www.clinicaltrialsregister.eu/ctr-search/trial/2020-002023-11/BG/.

* cited by examiner

XRPD pattern of the hemi (L)-tartrate form of rilematovir, Form 1

XRPD pattern of the hemi (L)-tartrate form of rilematovir, Form 2

XRPD pattern of the hemi (L)-tartrate form of rilematovir, Form 3

DSC thermogram of hemi (L)-tartrate form of rilematovir, Form 1

DSC thermogram of hemi (L)-tartrate form of rilematovir, Form 3

Solid state 19F-NMR spectrum of hemi (L)-tartrate from of rilematovir, Form 3

HEMI (L)-TARTRATE FORMS OF 3-({5-CHLORO-1-[3-(METHYLSULFONYL)PROPYL]-1H-INDOL-2-YL}METHYL)-1-(2,2,2-TRIFLUOROETHY)-1,3-DIHYDRO-2H-IMIDAZO[4,5-C]PYRIDIN-2-ONE AND PHARMACEUTICAL COMPOSITIONS COMPRISING THE SAME

CROSS-REFERENCE TO RELATED APPLICATIONS

This application claims priority to EP Patent Application No. 20179407.0, filed on Jun. 11, 2020, which is incorporated herein in its entirety.

The present invention relates to hemi (L)-tartrate forms of the RSV fusion inhibitor 3-({5-chloro-1-[3-(methylsulfonyl)propyl]-1H-indol-2-yl}methyl)-1-(2,2,2-trifluoroethyl)-1,3-dihydro-2H-imidazo[4,5-c]pyridin-2-one, and to processes for preparing said forms and the use of these forms in a pharmaceutical composition.

BACKGROUND

Respiratory syncytial virus is a major cause of acute lower respiratory tract infection in young children, immunocompromised adults, and the elderly. Intervention with small-molecule antivirals specific for respiratory syncytial virus presents an important therapeutic opportunity, but no such compound is approved today.

It is well recognized by those of skill in the art that oral liquid dosage forms, such as solutions, syrups and liquid suspensions, are highly preferable dosage forms for pediatric administration. Solid dosage forms such as tablets and capsules are difficult for children to swallow and the amount of drug administered cannot easily be adjusted in respect of the body weight. By contrast with liquid dosage forms the amount of drug delivered to the patient can be varied over a wide range merely by regulating the volume of dose of known concentrations of liquid dosage forms.

From the perspective of ease of use, accuracy of dose, and bioavailability, oral liquid dosage forms are generally preferred to be in the form of a solution. From the perspective of taste, oral liquid dosage forms are generally preferred to be in the form of a suspension which tends to mask the taste of the drug. This is very useful with pediatric treatments as children generally do not like the taste of medicines. If the taste is not pleasing, the child can spit it out and therefore affect the treatment regimen. Especially for pediatric use, where doses are relatively small, accuracy and precision of dose is extremely important. For this reason, the preferable oral liquid form for children is an oral suspension.

Such oral suspensions are not only useful in pediatric treatment but also in the treatment of adult patients who have difficulties in swallowing solid dosage forms.

Since liquid suspensions provide maximal dosing flexibility and the possibility to use a single formulation over a wide age range (including neonates), it is therefore an objective of the present invention to provide for an oral suspension comprising the RSV fusion inhibitor 3-({5-chloro-1-[3-(methylsulfonyl)propyl]-1H-indol-2-yl}methyl)-1-(2,2,2-trifluoroethyl)-1,3-dihydro-2H-imidazo[4,5-c]pyridin-2-one (i.e., Compound A, also known under its INN as rilematovir). It is a further objective of the present invention to provide a product comprising of a first pharmaceutical composition and a second pharmaceutical composition that can be reconstituted to an oral suspension. It is also an objective of the present invention to provide rilematovir in a form that is suitable for use in such oral suspensions.

PRIOR ART

The RSV fusion inhibitor 3-({5-chloro-1-[3-(methylsulfonyl)propyl]-1H-indol-2-yl}methyl)-1-(2,2,2-trifluoroethyl)-1,3-dihydro-2H-imidazo[4,5-c]pyridin-2-one, represented by the following structure:

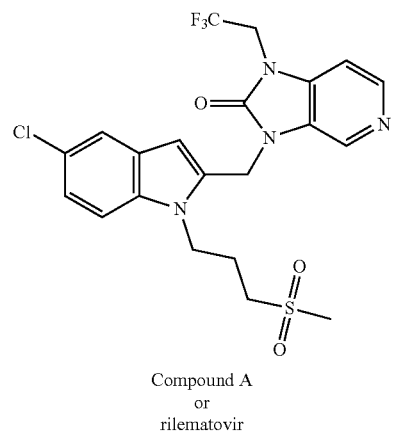 [SMILES: CS(=O)(=O)CCCn1c(Cn2c(=O)n(CC(F)(F)F)c3ccncc32)cc2cc(Cl)ccc21]

Compound A
or
rilematovir inhibits the replication of the respiratory syncytial virus (RSV) and has been described in WO-2012/080447 as compound P55. This compound is referenced to as 'Compound A' throughout this text. This compound is also known under its INN as rilematovir.

DESCRIPTION OF THE INVENTION

Figure 1:
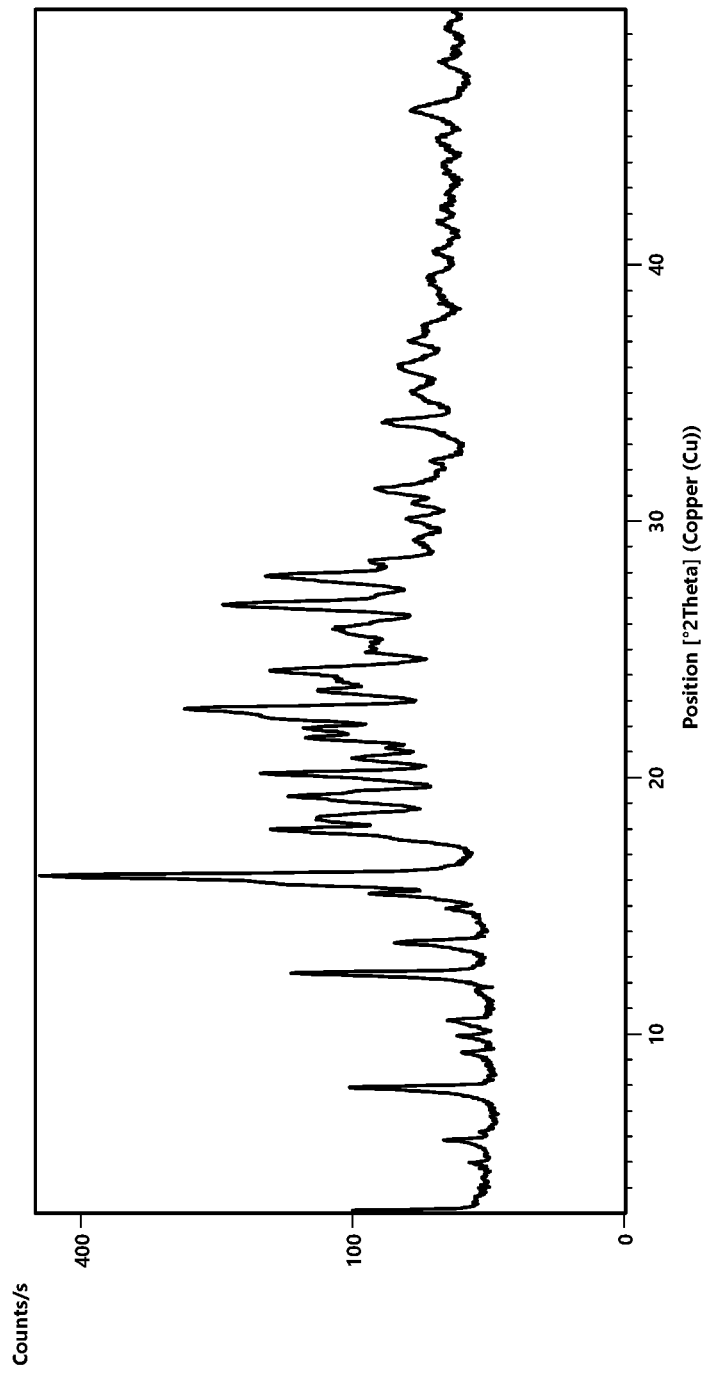
FIG. 1 X-ray powder diffraction pattern (XRPD) pattern of the hemi (L)-tartrate form of rilematovir, Form 1

Good bioavailability of an active pharmaceutical ingredient (API) is very important for successful treatment. The solubility of an API in human intestinal fluids and its intrinsic dissolution rate are considered suitable parameters to predict the bioavailability of said API.

It has now been found that the hemi (L)-tartrate form of rilematovir has an unexpected higher solubility in biorelevant media and an unexpected higher intrinsic dissolution rate compared to rilematovir in its free base form.

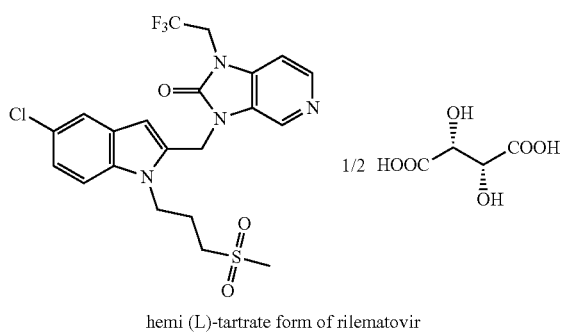 [SMILES: CS(=O)(=O)CCCn1c(Cn2c(=O)n(CC(F)(F)F)c3ccncc32)cc2cc(Cl)ccc21 ; O=C(O)[C@H](O)[C@@H](O)C(=O)O]

hemi (L)-tartrate form of rilematovir

The intrinsic dissolution rate (IDR) describes how fast a compound is released from its solid-state form into solution. The intrinsic dissolution rate is defined as the rate of dissolution of a pure active pharmaceutical ingredient when surface area, stirring speed, pH and ionic-strength of the dissolution medium are kept constant. Thus, it is measured as the release of API from a flat and well-defined surface area into an aqueous solution at a given pH value. By exposing the surface area of a material to an appropriate dissolution medium while maintaining constant temperature, stirring rate, and pH, the intrinsic dissolution rate can be determined. Typically the intrinsic dissolution is expressed in terms of mg per minute per $cm^2$.

Materials in solid state can be subdivided in many forms such as a, for example, crystalline, amorphous, salt, solvate, hydrate, and co-crystal forms. In salts, the components are arranged in the crystal lattice predominantly based on ion pairing. Although the detailed definition of co-crystals is still debated in the scientific literature, co-crystals are in general defined as homogenous (single phase) crystalline structures made up of two or more components in a definite stoichiometric ratio where the arrangement in the crystal lattice is not based on ionic bonds as with salts but via weaker interactions such as e.g. hydrogen bonding or van der Waals interactions. It is hypothesized the 'hemi (L)-tartrate form of rilematovir' is more likely to be classified as a co-crystal than a salt; however, in order not to be bound by a specific term or definition the more general wording 'form' has been used. An inherent risk with such forms when present in a liquid suspension is disproportionation whereby the association of components making up the form, in this case rilematovir and (L)-tartaric acid, dissociate into separate components.

Such disproportionation has to be avoided since the hemi (L)-tartrate form of rilematovir would then dissociate into rilematovir and (L)-tartaric acid and the advantageous properties of increased solubility and increased intrinsic dissolution rate for the hemi (L)-tartrate form in biorelevant fluids would be lost. It has now been found that when the hemi (L)-tartrate form of rilematovir is used in the liquid aqueous suspensions of the present invention, no disproportionation has been observed after storing these liquid suspensions for a period of 8 months in sealed glass vials at temperatures ranging from 30° C. to 50° C.

Consequently, the hemi (L)-tartrate form of rilematovir has the unexpected technical advantages of
higher solubility in biorelevant media compared to rilematovir in its free base form
higher intrinsic dissolution rate compared to rilematovir in its free base form
no disproportionation in liquid aqueous suspensions.

(L)-tartaric acid is also known as (L)-(+)-tartaric acid, (+)-tartaric acid, (2R,3R)-2,3-dihydroxysuccinic acid or (2R,3R)-2,3-dihydroxybutanedioic acid and throughout the description and claims "(L)-tartaric acid" has been used.

Throughout the description and claims of this specification, the words "comprise" and "contain" and variations of the words, for example "comprising" and "comprises", mean "including but not limited to", and are not intended to (and do not) exclude other components.

Polymorphic Forms

Certain compounds can exist in or form different polymorphic forms. As known in the art, polymorphism is an ability of a compound to crystallize as more than one distinct crystalline or "polymorphic" species. A polymorph is one solid crystalline phase of a compound that has at least two different arrangements or polymorphic forms in the solid state. Polymorphic forms of any given compound are defined by the same chemical formula or composition that are distinct in their crystalline structures and typically have different physico-chemical properties. Generally, different polymorphs can be characterized by analytical methods such as X-ray powder diffraction (XRPD), thermogravimetric analysis (TGA), and differential scanning calorimetry (DSC), melting point analysis, or other techniques known in the art.

For the purposes of this disclosure, the terms "crystalline form" and "polymorph" are synonymous. Characterizing information for crystalline forms is provided herein. It should be understood that the determination of a particular form can be achieved using any portion of the characterizing information that one skilled in the art would recognize as sufficient for establishing the presence of a particular form. For example, even a single distinguishing peak can be sufficient for one skilled in the art to appreciate that a particular form is present.

When a crystalline form is identified using one or more XRPD peaks given as angles 2θ (two theta), each of the 2θ values is understood to mean the given value±0.2 degrees, unless otherwise expressed.

The term "seeding" refers to the addition of crystalline material to a solution or mixture to initiate crystallisation or recrystallisation. Seeding material can be obtained by spontaneous crystallization.

Polymorph Form 1 of the Hemi (L)-Tartrate Form of Rilematovir.

The polymorph Form 1 of the hemi (L)-tartrate form of rilematovir was prepared by dissolving rilematovir and L-tartaric acid in MEK (methyl ethyl ketone) at a temperature of 75° C. to 77° C., cooling the resulting solution to 67° C. and adding seeding material. After slowly cooling to 5° C., the crystalline hemi (L)-tartrate form of rilematovir was isolated by filtration.

The polymorph Form 1 of the hemi (L)-tartrate form of rilematovir may be characterized by an X-ray powder diffraction pattern. The X-ray powder diffraction pattern may be obtained using copper K-alpha (Cu Kα) X-rays at a wavelength of 1.5406.

The X-ray powder diffraction pattern of polymorph Form 1 of the hemi (L)-tartrate form of rilematovir comprises peaks at 16.2, 22.7 and 26.7 degrees two theta±0.2 degrees two theta. The X-ray powder diffraction pattern may further comprise peaks at 12.4, 15.8, 18.0 and 20.2 degrees two theta±0.2 degrees two theta. The X-ray powder diffraction pattern may even further comprise peaks at 19.2, 22.3, 24.2 and 27.9 degrees two theta±0.2 degrees two theta.

Additionally, or alternatively, the invention concerns a crystalline hemi (L)-tartrate form of rilematovir wherein the crystalline form is Form 1, characterized by an X-ray powder diffraction pattern comprising peaks at 12.4, 15.8, 16.2, 18.0, 20.2, 22.7, and 26.7 degrees two theta±0.2 degrees two theta when measured using Cu Kα radiation.

Additionally, or alternatively, the invention concerns a crystalline hemi (L)-tartrate form of rilematovir wherein the crystalline form is Form 1, characterized by an X-ray powder diffraction pattern comprising peaks at 7.9, 12.4, 15.8, 16.2, 18.0, 18.5, 19.3, 20.2, 21.9, 22.3, 22.7, 24.2, 26.7, and 27.9 degrees two theta±0.2 degrees two theta when measured using Cu Kα radiation.

Additionally, or alternatively, the invention concerns a crystalline hemi (L)-tartrate form of rilematovir wherein the crystalline form is Form 1, characterized by an X-ray powder diffraction pattern comprising peaks at 3.1, 7.9, 12.4, 13.5, 15.5, 15.8, 16.2, 18.0, 18.5, 19.3, 19.5, 20.2, 20.8, 21.6, 21.9, 22.3, 22.7, 23.4, 24.2, 25.8, 26.7, and 27.9 when measured using Cu Kα radiation.

Form 1 may further be characterized by an X-ray powder diffraction pattern having five, six, seven, eight, nine, ten, eleven, twelve or more peaks selected from those peaks identified in Peak list 1.

Form 1 may further be characterized by an X-ray powder diffraction pattern comprising those peaks identified in Peak list 1, wherein the relative intensity of the peaks is greater than about 2%, preferably greater than about 5%, more preferably greater than about 10%, more preferably greater than about 15%.

Form 1 may further be characterized by a X-ray powder diffraction pattern substantially as depicted in FIG. 1.

The polymorph Form 1 of the hemi (L)-tartrate form of rilematovir may also be characterized by a differential scanning calorimetry (DSC) thermogram comprising a endothermic peak with onset temperature around 205.2° C.-206.1° C. and peak temperature around 206.3-206.9° C.

Figure 6:
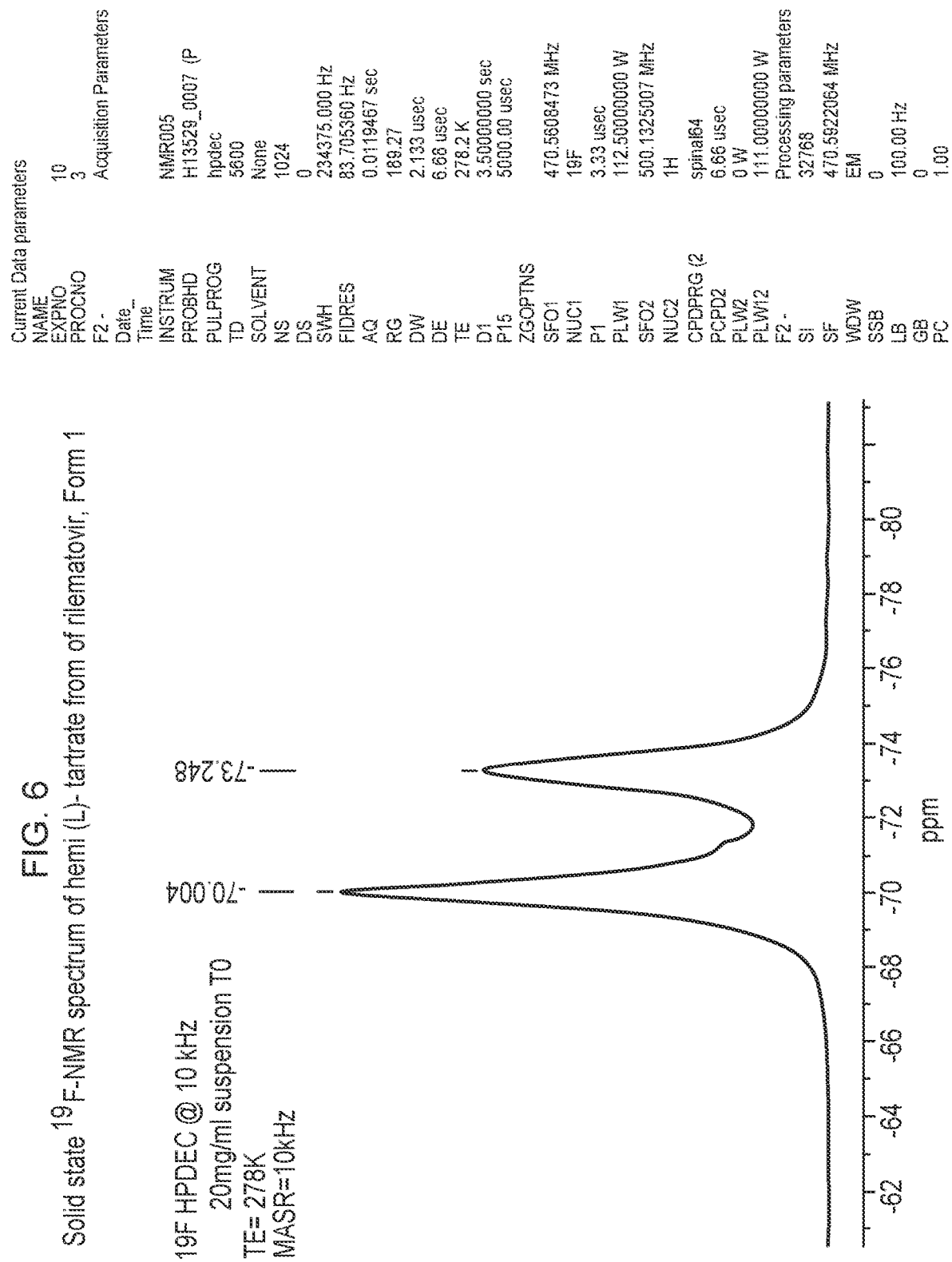
FIG. 6 Solid state $^{19}$F-NMR spectrum of hemi (L)-tartrate form of rilematovir, Form 1

The polymorph Form 1 of the hemi (L)-tartrate form of rilematovir may also be characterized by solid state $^{19}$F-NMR spectroscopy. FIG. 6 is the solid state $^{19}$F-NMR spectrum of an oral suspension as prepared in accordance with Example 10 and recorded immediately after the suspension was prepared. The polymorph Form 1 has peaks at −70.004 ppm and −73.248 ppm. Additionally, or alternatively, the invention concerns a crystalline hemi (L)-tartrate form of rilematovir wherein the crystalline form is Form 1, characterized by a solid state $^{19}$F-NMR spectrum comprising peaks at about −70 ppm and −73.2 ppm.

Additional data from $^{15}$N ssNMR and X-ray crystallography with synchrotron radiation indicate that polymorph Form 1 can be classified as a co-crystal.

In an embodiment the present invention provides a process for the preparation of the polymorph Form 1 of the hemi (L)-tartate form of rilematovir comprising the steps of crystallizing a hemi (L)-tartate form of rilematovir from a solvent selected from the group consisting of acetone, acetonitrile, 2-propanol, methyl ethyl ketone, and THF, and mixtures thereof. Crystallization may comprise cooling from elevated temperature. Preferably the solvent is methyl ethyl ketone.

Polymorph Form 2 of the Hemi (L)-Tartrate Form of Rilematovir.

The polymorph Form 2 of the hemi (L)-tartrate form of rilematovir was prepared by heating the polymorph Form 1 in cyclohexanone up to a temperature of 85° C. at a heating rate of 10° C./min and keeping it isothermal for 5 minutes. After cooling to room temperature, the crystalline hemi (L)-tartrate form of rilematovir was isolated by filtration.

The polymorph Form 2 of the hemi (L)-tartrate form of rilematovir may be characterized by an X-ray powder diffraction pattern. The X-ray powder diffraction pattern may be obtained using copper K-alpha (Cu Kα) X-rays at a wavelength of 1.5406.

The X-ray powder diffraction pattern of polymorph Form 2 of the hemi (L)-tartrate form of rilematovir comprises peaks at 14.4, 16.4 and 19.0 degrees two theta±0.2 degrees two theta. The X-ray powder diffraction pattern may further comprise peaks at 14.7, 17.1, 19.4 and 20.7 degrees two theta±0.2 degrees two theta. The X-ray powder diffraction pattern may even further comprise peaks at 14.1, 18.4, 21.7 and 22.6 degrees two theta±0.2 degrees two theta.

Additionally, or alternatively, the invention concerns a crystalline hemi (L)-tartrate form of rilematovir wherein the crystalline form is Form 2, characterized by an X-ray powder diffraction pattern comprising peaks at 14.4, 14.7, 16.4, 17.1, 19.0, 19.4, and 20.7 degrees two theta±0.2 degrees two theta when measured using Cu Kα radiation.

Additionally, or alternatively, the invention concerns a crystalline hemi (L)-tartrate form of rilematovir wherein the crystalline form is Form 2, characterized by an X-ray powder diffraction pattern comprising peaks at 14.1, 14.4, 14.7, 16.4, 17.1, 18.4, 19.0, 19.4, 20.7, 21.7, 22.6, 23.5, 27.3, and 27.8 degrees two theta±0.2 degrees two theta when measured using Cu Kα radiation.

Additionally, or alternatively, the invention concerns a crystalline hemi (L)-tartrate form of rilematovir wherein the crystalline form is Form 2, characterized by an X-ray powder diffraction pattern comprising peaks at 5.2, 7.1, 14.1, 14.4, 14.7, 15.6, 16.4, 17.1, 18.4, 19.0, 19.4, 20.7, 21.7, 22.6, 23.5, 24.0, 24.8, 25.6, 26.3, 26.9, 27.3, 27.8, 28.8, 29.4, and 29.9 when measured using Cu Kα radiation.

Form 2 may further be characterized by an X-ray powder diffraction pattern having five, six, seven, eight, nine, ten, eleven, twelve or more peaks selected from those peaks identified in Peak list 2.

Form 2 may further be characterized by an X-ray powder diffraction pattern comprising those peaks identified in Peak list 2 wherein the relative intensity of the peaks is greater than about 2%, preferably greater than about 5%, more preferably greater than about 10%, more preferably greater than about 15%.

Figure 2:
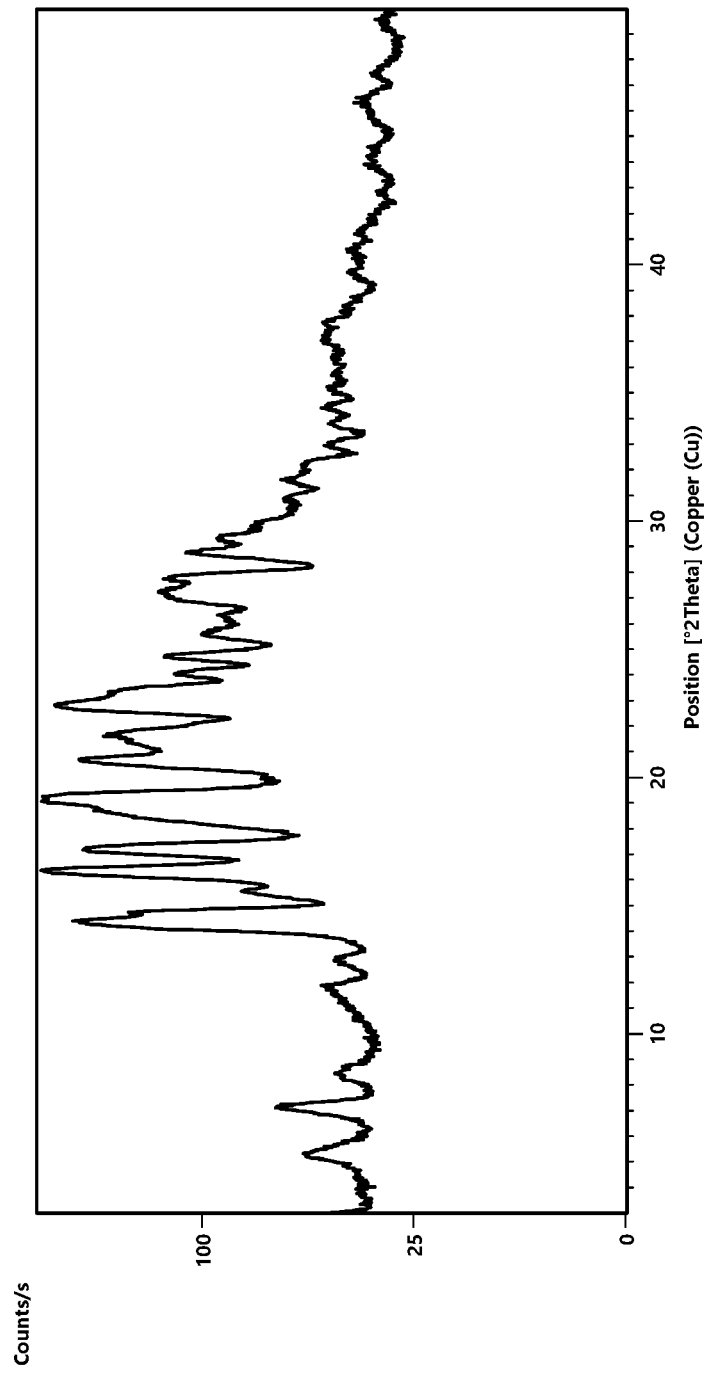
FIG. 2 X-ray powder diffraction pattern (XRPD) pattern of the hemi (L)-tartrate form of rilematovir, Form 2

Form 2 may further be characterized by a X-ray powder diffraction pattern substantially as depicted in FIG. 2.

Polymorph Form 3 of the hemi (L)-tartrate form of rilematovir.

The polymorph Form 3 of the hemi (L)-tartrate form of rilematovir was found during aging testing of the liquid aqueous suspensions comprising Form 1 of the hemi (L)-tartrate form of rilematovir. It was observed that over time Form 1 converts into Form 3.

The polymorph Form 3 of the hemi (L)-tartrate form of rilematovir may be characterized by an X-ray powder diffraction pattern. The X-ray powder diffraction pattern may be obtained using copper K-alpha (Cu Kα) X-rays at a wavelength of 1.5406.

The X-ray powder diffraction pattern of polymorph Form 3 of the hemi (L)-tartrate form of rilematovir comprises peaks at 16.2, 16.5 and 18.8 degrees two theta±0.2 degrees two theta. The X-ray powder diffraction pattern may further comprise peaks at 12.2, 15.3, 15.5 and 24.6 degrees two theta±0.2 degrees two theta. The X-ray powder diffraction pattern may even further comprise peaks at 12.4, 20.6, 21.8 and 28.6 degrees two theta±0.2 degrees two theta.

Additionally, or alternatively, the invention concerns a crystalline hemi (L)-tartrate form of rilematovir wherein the crystalline form is Form 3, characterized by an X-ray powder diffraction pattern comprising peaks at 8.2, 12.2, 15.3, 15.5, 16.2, 16.5, and 18.8 degrees two theta±0.2 degrees two theta when measured using Cu Kα radiation.

Additionally, or alternatively, the invention concerns a crystalline hemi (L)-tartrate form of rilematovir wherein the crystalline form is Form 3, characterized by an X-ray powder diffraction pattern comprising peaks at 8.2, 12.2, 12.4, 15.3, 15.5, 16.2, 16.5, 17.0, 18.8, 20.6, 21.8, 23.2, 24.6, and 27.4 degrees two theta±0.2 degrees two theta when measured using Cu Kα radiation.

Additionally, or alternatively, the invention concerns a crystalline hemi (L)-tartrate form of rilematovir wherein the crystalline form is Form 3, characterized by an X-ray powder diffraction pattern comprising peaks at 7.7, 8.2, 12.2, 12.4, 14.2, 15.3, 15.5, 16.2, 16.5, 17.0, 17.4, 18.8, 20.4, 20.6, 21.8, 22.5, 23.2, 24.6, 26.1, 26.9, 27.4, 27.9, 28.6, 31.0, 32.8, and 34.2 when measured using Cu Kα radiation.

Form 3 may further be characterized by an X-ray powder diffraction pattern having five, six, seven, eight, nine, ten, eleven, twelve or more peaks selected from those peaks identified in Peak list 3.

Form 3 may further be characterized by an X-ray powder diffraction pattern comprising those peaks identified in Peak list 3, wherein the relative intensity of the peaks is greater than about 2%, preferably greater than about 5%, more preferably greater than about 10%, more preferably greater than about 15%.

Figure 3:
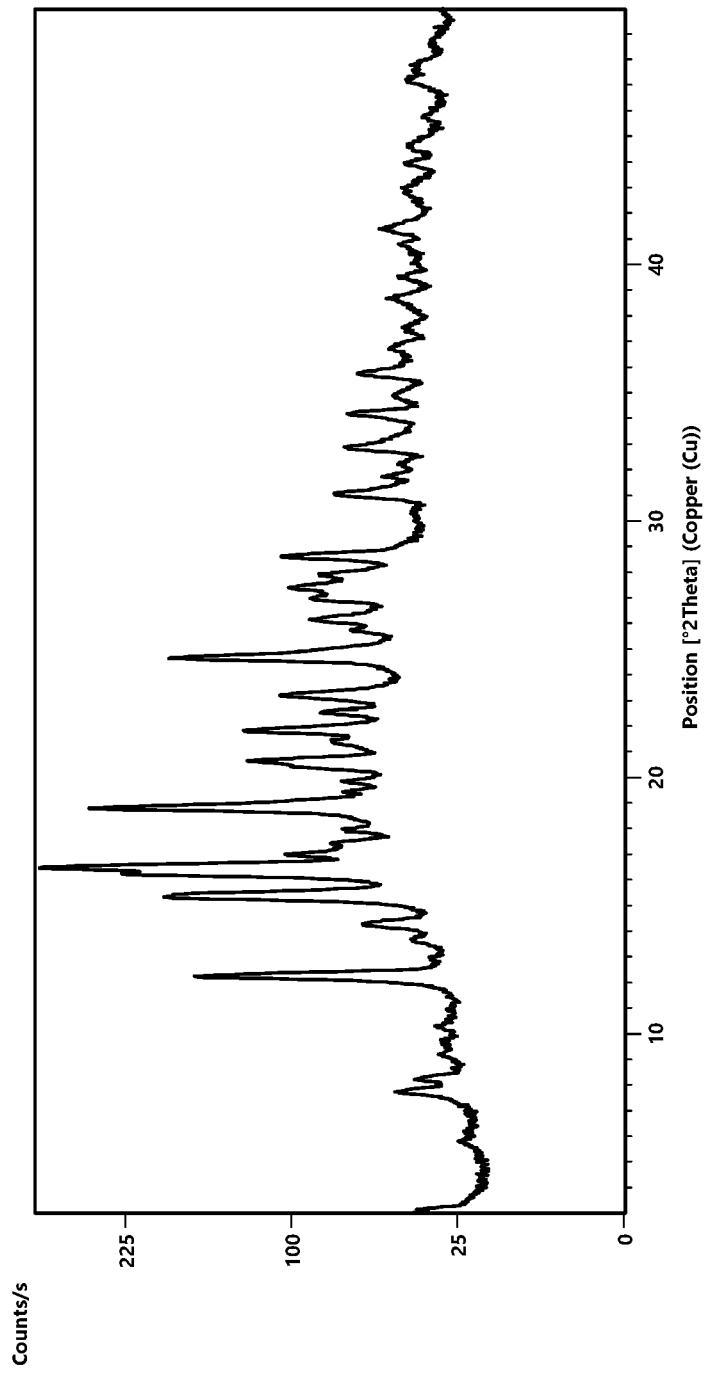
FIG. 3 X-ray powder diffraction pattern (XRPD) pattern of the hemi (L)-tartrate form of rilematovir, Form 3

Form 3 may further be characterized by a X-ray powder diffraction pattern substantially as depicted in FIG. 3.

The polymorph Form 3 of the hemi (L)-tartrate form of rilematovir may also be characterized by a differential scanning calorimetry (DSC) thermogram comprising an endothermic peak with onset temperature around 201.4° C.-201.7° C. and peak temperature around 204.3-205.0° C. Since Form 3 was obtained through the conversion of Form 1 in aqueous suspensions comprising HPMC (see Example 3), all samples of isolated Form 3 invariably comprise a small amount of HPMC which may have an effect on its melting point in DSC experiments.

Figure 7:
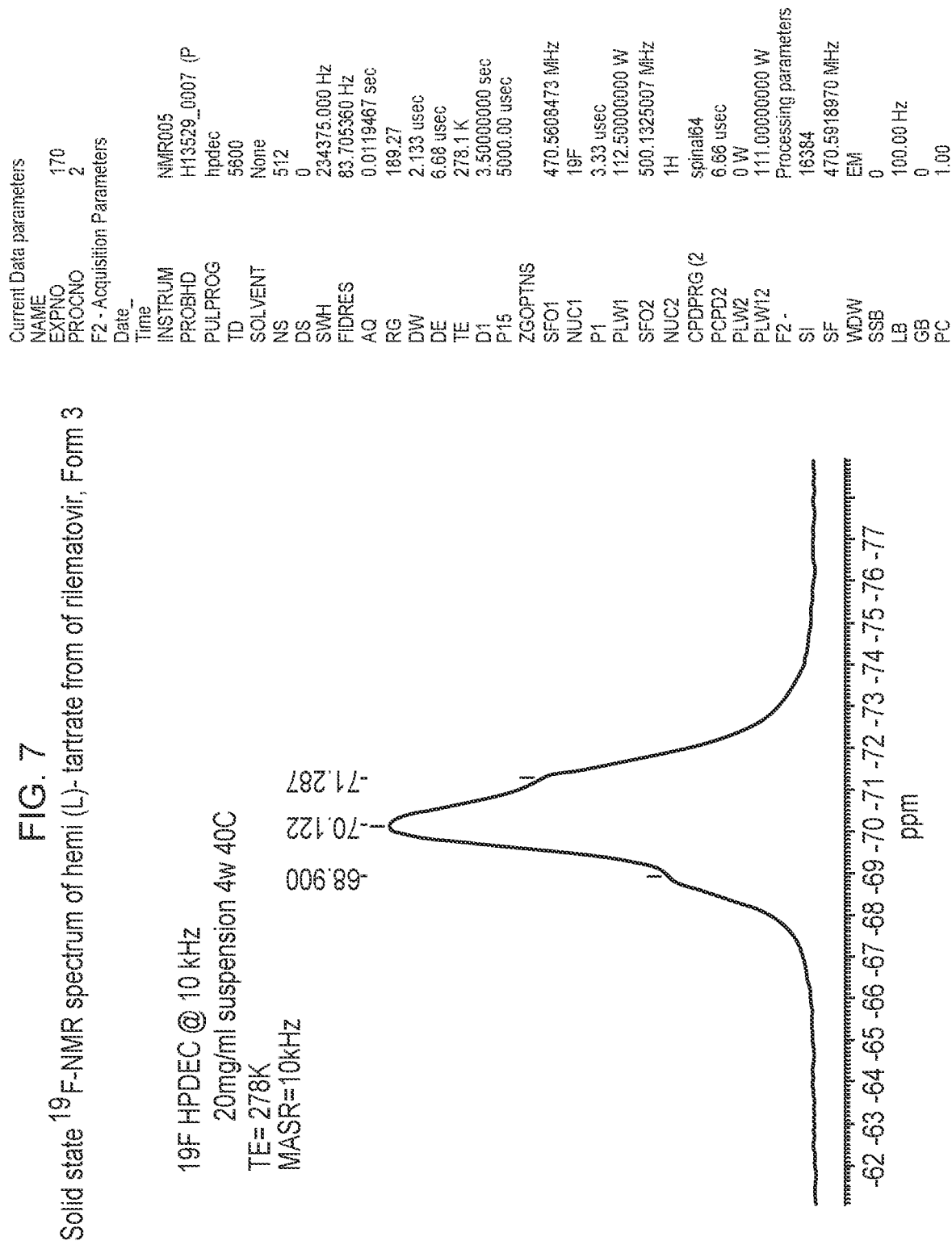
FIG. 7 Solid state $^{19}$F-NMR spectrum of hemi (L)-tartrate form of rilematovir, Form 3

The polymorph Form 3 of the hemi (L)-tartrate form of rilematovir may also be characterized by solid state $^{19}$F-NMR spectroscopy. FIG. 7 is the solid state $^{19}$F-NMR spectrum of an oral suspension as prepared in accordance with Example 10 and recorded 4 weeks after the suspension was prepared and stored at 40° C. The polymorph Form 3 has a peak at −70.122 ppm. Additionally, or alternatively, the invention concerns a crystalline hemi (L)-tartrate form of rilematovir wherein the crystalline form is Form 3, characterized by a solid state $^{19}$F-NMR spectrum comprising a peak at about −70.1 ppm.

Additional data from $^{15}$N ssNMR and X-ray crystallography with synchrotron radiation indicate that polymorph Form 3 can be classified as a co-crystal.

In an aspect, provided herein is a hemi (L)-tartrate form of rilematovir for use in the treatment or prophylaxis of a respiratory syncytial virus (RSV) infection in a patient. In a further aspect, the hemi (L)-tartrate form of rilematovir is selected from the group consisting of polymorph Form 1, Form 2 and Form 3, and mixtures thereof, such as a mixture of polymorph Form 1 and Form 3.

In another aspect, provided herein is the use of a hemi (L)-tartrate form of rilematovir for the manufacture of a medicament for the treatment or prophylaxis of a respiratory syncytial virus (RSV) infection in a patient. In a further aspect, the hemi (L)-tartrate form of rilematovir is selected from the group consisting of polymorph Form 1, Form 2 and Form 3, and mixtures thereof, such as a mixture of polymorph Form 1 and Form 3.

In another aspect, provided herein is a method for the treatment or prophylaxis of respiratory syncytial virus infection or a condition caused by respiratory syncytial virus infection, which method comprises administering a therapeutically effective amount of a hemi (L)-tartrate form of rilematovir or the pharmaceutical composition disclosed herein. In a further aspect, the hemi (L)-tartrate form of rilematovir is selected from the group consisting of polymorph Form 1, Form 2 and Form 3, and mixtures thereof, such as a mixture of polymorph Form 1 and Form 3.

Pharmaceutical Compositions.

In an aspect it is an objective of the present invention to provide for a pharmaceutical composition comprising a hemi (L)-tartrate form of rilematovir. In a further aspect, the hemi (L)-tartrate form of rilematovir is selected from the group consisting of polymorph Form 1, Form 2 and Form 3, and mixtures thereof, such as a mixture of polymorph Form 1 and Form 3.

The pharmaceutical compositions may be provided in liquid form, or may be provided in dry form (for example granule or powder) to which an appropriately formulated aqueous solvent is added to provide a liquid aqueous suspension of this invention. Ingredients suitable for liquid aqueous suspensions are known and such a formulation may be made by methods known in the art.

Additionally, or alternatively, the pharmaceutical composition is a liquid aqueous suspension comprising a hemi (L)-tartrate form of rilematovir. Additionally, or alternatively, the hemi (L)-tartrate form of rilematovir is selected from the group consisting of polymorph Form 1, Form 2 and Form 3, and mixtures thereof, such as a mixture of polymorph Form 1 and Form 3.

The liquid suspensions according to the present invention comprise
a) a hemi (L)-tartrate form of rilematovir in a concentration from 5 mg/mL to 100 mg/mL,
b) (L)-tartaric acid,
c) a suspending agent,
d) optional excipients,
e) water, and
f) wherein the pH ranges from 2.8 to 3.6.

The concentration of hemi (L)-tartrate form of rilematovir in the liquid forms or liquid aqueous suspensions ranges from 5 mg/mL to 100 mg/mL. This concentration is dependent upon the patient population targeted for the treatment of RSV infection. For pediatric treatment, the concentration of hemi (L)-tartrate form of rilematovir ranges from 5 mg/mL to 30 mg/mL. Additionally, or alternatively, the concentration of hemi (L)-tartrate form of rilematovir is approximately 5.7 mg/mL, 11.5 mg/mL or 23 mg/mL which is the equivalent of 5 mg/mL, 10 mg/mL or 20 mg/mL of rilematovir in its free base form. For the treatment of adults, the concentration of hemi (L)-tartrate form of rilematovir ranges from 20 mg/mL to 100 mg/mL. Additionally, or alternatively, the concentration of hemi (L)-tartrate form of rilematovir is approximately 23 mg/mL or 57.5 mg/mL which is the equivalent of 20 mg/mL or 50 mg/mL of rilematovir in its free base form.

The concentration of (L)-tartaric acid in the liquid forms, or liquid aqueous suspensions, ranges from 5 to 10 mg/mL, in particular approximately 7.5 mg/mL. Said concentration of (L)-tartaric acid does not include any amount of (L)-tartaric acid that is present in the hemi (L)-tartrate form of rilematovir. The (L)-tartaric acid in the liquid acts as a buffer for the aqueous suspension and the pH of the suspension can be adjusted by adding a base.

The pH of the liquid aqueous suspensions of the present invention is adjusted with a base, preferably sodium hydroxide, to a pH ranging from 2.8 to 3.6; preferably the pH is 3.2.

Suspending agents, also called thickening agents, are used in liquid aqueous suspensions to help the active pharmaceutical ingredients stay suspended in the formulation and to prevent caking at the bottom of the container. The most common suspending agents are colloidal anhydrous silica, aqueous biological polymers, including methylcellulose (MC), microcrystalline cellulose, sodium carboxymethylcellulose (CMC), carrageenan, xanthan gum, and hydroxypropylmethylcellulose (HPMC). A particular thickening agent is HPMC such as HPMC E5, or HPMC 2910. The concentration of the suspending agent in the liquid forms, or the liquid suspensions, ranges from 10 mg/mL to 100 mg/mL, from 20 mg/mL to 100 mg/mL, from 30 mg/mL to 100 mg/mL, or from 40 mg/mL to 80 mg/mL or from 45 mg/mL to 60 mg/mL.

The optional excipients are for example preservatives, sweeteners, anti-foaming agents, flavouring agents, pH adjusting agents, wetting agents, and the like, or a combination thereof.

Preservatives may be included in pharmaceutical formulations to kill or inhibit the growth of micro-organisms inadvertently introduced during manufacture or use. The choice of a suitable preservative for a formulation depends on pH, compatibility with other ingredients, the route of administration, dose and frequency of administration of the formulation, partition coefficients with ingredients and containers or closures, degree and type of contamination, concentration required, and rate of antimicrobial effect. Art-known preservatives are, e.g., parabens such as methylparaben, sodium methyl paraben, ethylparaben, sodium ethylparaben, propylparaben, sodium propylparaben, butylparaben, or sodium butylparaben, benzoic acid, sorbic acid, acetic acid, propionic acid, sodium propionate, propylene glycol, ethyl alcohol, benzyl alcohol, sodium benzoate, potassium sorbate, or disodium edetate.

Anti-foaming agents are used to prevent or reduce foaming of the liquid aqueous suspensions of the invention when such suspensions have been shaken. Well-known anti-foaming agents are simethicone and dimethicone.

The sweetener can be an intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), or a bulk sweetener such as sorbitol, mannitol, fructose, sucrose, maltose, isomalt, glucose, hydrogenated glucose syrup, xylitol, caramel or honey. The sweetener can also be a combination of one or more intense sweeteners and/or one or more bulk sweeteners.

The flavour can be a fruit flavour such as cherry, raspberry, black currant, or strawberry flavour, or caramel chocolate flavour, mint cool flavour, fantasy flavour and the like pharmaceutically acceptable strong flavours. Preferably a flavour is used that does not undergo any change or loss of taste and colour under the acidic conditions of the formulation.

Additionally, or alternatively, the invention provides a liquid suspension comprising
a) a hemi (L)-tartrate form of rilematovir in a concentration from 5 mg/mL to 100 mg/mL,
b) (L)-tartaric acid,
c) a suspending agent,
d) optional excipients,
e) water, and
f) wherein the pH ranges from 2.8 to 3.6.

Additionally, or alternatively, the invention provides a liquid suspension comprising
a) a hemi (L)-tartrate form of rilematovir in a concentration from 5 mg/mL to 100 mg/mL,
b) (L)-tartaric acid in a concentration ranging from 5 to 10 mg/mL,
c) a suspending agent in a concentration ranging from 10 mg/mL to 100 mg/mL,
d) optional excipients,
e) water, and
f) wherein the pH ranges from 2.8 to 3.6.

Additionally, or alternatively, the invention provides a liquid suspension comprising
a) a hemi (L)-tartrate form of rilematovir in a concentration from 5 mg/mL to 30 mg/mL or from 30 mg/mL to 80 mg/mL,
b) (L)-tartaric acid in a concentration ranging from 5 to 10 mg/mL,
c) a suspending agent in a concentration ranging from 10 mg/mL to 100 mg/mL, wherein the suspending agent is selected from the group consisting of colloidal anhydrous silica, methylcellulose, microcrystalline cellulose, sodium carboxymethylcellulose, carrageenan, xanthan gum, and hydroxypropylmethylcellulose,
d) optional excipients,
e) water, and
f) wherein the pH ranges from 2.8 to 3.6.

Additionally, or alternatively, the present invention provides a liquid suspension comprising
a) a hemi (L)-tartrate form of rilematovir in a concentration of 5.7 mg/mL,
b) (L)-tartaric acid in a concentration of 7.5 mg/mL,
c) a suspending agent in a concentration ranging from 45 mg/mL to 60 mg/mL, wherein the suspending agent is hydroxypropylmethylcellulose,
d) optional excipients,
e) water, and
f) wherein the pH ranges from 2.8 to 3.6.

Additionally, or alternatively, the present invention provides a liquid suspension comprising
a) a hemi (L)-tartrate form of rilematovir in a concentration of 11.5 mg/mL,
b) (L)-tartaric acid in a concentration of 7.5 mg/mL,
c) a suspending agent in a concentration ranging from 45 mg/mL to 60 mg/mL, wherein the suspending agent is hydroxypropylmethylcellulose,
d) optional excipients,
e) water, and
f) wherein the pH ranges from 2.8 to 3.6.

Additionally, or alternatively, the present invention provides a liquid suspension comprising
a) a hemi (L)-tartrate form of rilematovir in a concentration of 23 mg/mL,
b) (L)-tartaric acid in a concentration of 7.5 mg/mL,
c) a suspending agent in a concentration ranging from 45 mg/mL to 60 mg/mL, wherein the suspending agent is hydroxypropylmethylcellulose,
d) optional excipients,
e) water, and
f) wherein the pH ranges from 2.8 to 3.6.

Additionally, or alternatively, the present invention provides a liquid suspension comprising
a) a hemi (L)-tartrate form of rilematovir in a concentration of 57.5 mg/mL, b) (L)-tartaric acid in a concentration of 7.5 mg/mL,
c) a suspending agent in a concentration ranging from 45 mg/mL to 60 mg/mL, wherein the suspending agent is hydroxypropylmethylcellulose,
d) optional excipients,
e) water, and
f) wherein the pH ranges from 2.8 to 3.6.

Additionally, or alternatively, the optional excipients are present as preservatives, sweeteners, anti-foaming agents, flavouring agents, pH adjusting agents, wetting agents and buffers.

In any of the above liquid suspensions, the hemi (L)-tartrate form of rilematovir is selected from the group consisting of polymorph Form 1, Form 2 and Form 3, and mixtures thereof. In one aspect, the hemi (L)-tartrate form of rilematovir is of Form 1. Additionally, or alternatively, the hemi (L)-tartrate form of rilematovir is of Form 3. Additionally, or alternatively, the hemi (L)-tartrate form of rilematovir is a mixture of Form 1 and Form 3.

The liquid aqueous suspension according to the present invention can also be made in a form that can be reconstituted before use. Accordingly the present invention also provides a pharmaceutical product comprising of a first pharmaceutical composition that comprises a hemi (L)-tartrate form of rilematovir and of a second pharmaceutical composition that comprises a pharmaceutical diluent whereby the first and second pharmaceutical composition can be mixed and thereby reconstituted to obtain a liquid aqueous suspension of the invention. Additionally, or alternatively, the hemi (L)-tartrate form of rilematovir is selected from the group consisting of polymorph Form 1, Form 2 and Form 3, and mixtures thereof, such as a mixture of polymorph Form 1 and Form 3.

The present invention also provides a pharmaceutical product comprising of a first pharmaceutical composition and a second pharmaceutical composition wherein the first pharmaceutical composition comprises
a) a hemi (L)-tartrate form of rilematovir in a concentration from 20% (w/w) to 100% (w/w), and
b) a bulking agent to make up to 100% (w/w);
and
the second pharmaceutical composition comprises
c) (L)-tartaric acid,
d) a suspending agent,
e) optional excipients,
f) water, and
g) wherein the pH ranges from 2.8 to 3.6.

A bulking agent is an additive placed in powdered or granulated materials to improve overall handling characteristics such as, e.g., flowability of the powdered materials, reduction or prevention of clumping and caking, reduction or prevention of material sticking to the receptacle in which it is stored. When small amounts of the powdered materials need to be handled, such as, e.g., filling an exact amount in a glass bottle at an industrial level where both accuracy and speed are important, the addition of a bulking agents increases the overall amount of solid material and increases the accuracy of weighing and dispensing. Well-known bulking agents are, for example, powdered cellulose, magnesium stearate, sodium bicarbonate, sodium silicate, silicon dioxide, fumed silica, bentonite, stearic acid, polydimethylsiloxane, mannitol, and the like, or a combination thereof. The bulking agent used in the first pharmaceutical composition can also be a combination of more than one bulking agent such as a combination of mannitol and silicon dioxide.

Additionally, or alternatively, the pharmaceutical product according to the present invention comprises a first pharmaceutical composition comprising
a) a hemi (L)-tartrate form of rilematovir in a concentration from 20% (w/w) to 100% (w/w), and
b) a bulking agent to make up to 100% (w/w).

It will be understood by the skilled person that when the concentration of the hemi (L)-tartrate form of rilematovir in the first pharmaceutical composition is 100% (w/w) no bulking agent will be present.

Additionally, or alternatively, the pharmaceutical product according to the present invention comprises a first pharmaceutical composition comprising
a) a hemi (L)-tartrate form of rilematovir in a concentration from 20% (w/w) to 80% (w/w), and
b) a bulking agent to make up to 100% (w/w) selected from mannitol and silicon dioxide, or a combination thereof.

The composition of the second pharmaceutical composition is analogous to the liquid aqueous suspensions as described above.

Hence the pharmaceutical product according to the present invention comprises a second pharmaceutical composition comprising
a) (L)-tartaric acid,
b) a suspending agent,
c) optional excipients,
d) water, and
e) wherein the pH ranges from 2.8 to 3.6.

Additionally, or alternatively, the pharmaceutical product according to the present invention comprises a second pharmaceutical composition comprising
a) (L)-tartaric acid in a concentration ranging from 5 to 10 mg/mL,
b) a suspending agent in a concentration ranging from 10 mg/mL to 100 mg/mL,
c) optional excipients,
d) water, and
e) wherein the pH ranges from 2.8 to 3.6.

Additionally, or alternatively, the pharmaceutical product according to the present invention comprises a second pharmaceutical composition comprising
a) (L)-tartaric acid in a concentration ranging from 5 to 10 mg/mL,
b) a suspending agent in a concentration ranging from 10 mg/mL to 100 mg/mL, wherein the suspending agent is selected from the group consisting of colloidal anhydrous silica, methylcellulose, microcrystalline cellulose, sodium carboxymethylcellulose, carrageenan, xanthan gum, and hydroxypropylmethylcellulose,
c) optional excipients,
d) water, and
e) wherein the pH ranges from 2.8 to 3.6.

Additionally, or alternatively, the pharmaceutical product according to the present invention comprises a second pharmaceutical composition comprising
a) (L)-tartaric acid in a concentration of 7.5 mg/mL,
b) a suspending agent in a concentration ranging from 45 mg/mL to 60 mg/mL, wherein the suspending agent is hydroxypropylmethylcellulose,
c) optional excipients,
d) water, and
e) wherein the pH ranges from 2.8 to 3.6.

In any of the above pharmaceutical compositions, the hemi (L)-tartrate form of rilematovir is selected from the group consisting of polymorph Form 1, Form 2 and Form 3, or a mixture thereof, such as a mixture of polymorph Form 1 and Form 3. In one aspect, the hemi (L)-tartrate form of rilematovir is of Form 1. In another aspect the hemi (L)-tartrate form of rilematovir is of Form 3.

In the pharmaceutical product of the present invention—suitable for reconstituting to a liquid aqueous suspension–the first pharmaceutical composition that comprises the hemi (L)-tartrate form of rilematovir can be stored in a glass bottle, HDPE bottle, PET bottle, sachet, laminated stick pack, and the like. The second pharmaceutical composition that is the aqueous diluent can be stored in a glass bottle, HDPE bottle, PET bottle, and the like.

The liquid aqueous suspensions—either reconstituted or ready-for-use—of this invention are suitable for oral administration. For example the liquid aqueous suspensions may be taken in measured doses using a cup, straw, spoon, syringe, or other device. A preferred way of administering the liquid aqueous suspensions is using a syringe. Administration using a syringe can be done orally or through a nasogastric tube (NG tube).

The liquid aqueous suspensions of the present invention that are ready-for-use can be prepared by mixing the hemi (L)-tartrate form of rilematovir with the further excipients in an aqueous diluent using conventional procedures for mixing or suspension.

The liquid aqueous suspensions of the present invention can also be made by reconstituting powders, granules, pellets, sprinkles, dispersible tablets or lyophilized preparations. Reconstituting the liquid aqueous suspensions may be done from freely flowing powder in a suitable container. This freely flowing powder is added to the diluent (or vice versa) and the resulting suspension is shaken vigorously.

Additionally, or alternatively, the present invention also provides a kit comprising a first pharmaceutical composition and a second pharmaceutical composition of any one of the previous clauses and instructions for reconstituting both into a liquid aqueous suspension formulation; and optionally a container for reconstituting.

In an aspect, provided herein is a pharmaceutical composition of the invention comprising a hemi (L)-tartrate form of rilematovir for use in the treatment or prophylaxis of a respiratory syncytial virus (RSV) infection in a patient. Additionally, or alternatively, provided herein is a pharmaceutical composition of the invention comprising a hemi (L)-tartrate form of rilematovir for use in the treatment of a patient suffering from moderate to severe infection by respiratory syncytial virus (RSV). In a further aspect, the hemi (L)-tartrate form of rilematovir is selected from the group consisting of Form 1, Form 2 and Form 3, and mixtures thereof, such as a mixture of polymorph Form 1 and Form 3.

'Moderate' or 'severe' infection by respiratory syncytial virus (RSV) is defined as the presence of at least two lower respiratory tract diseases or conditions such as cough, wheeze, coughing up phlegm and short of breath. At least one of these symptoms is scored as moderate—for a moderate infection—or severe—for a severe infection—on an ordinal symptom score system as rated by a caregiver or physician.

In another aspect, provided herein is the use of a pharmaceutical composition of the invention comprising a hemi (L)-tartrate form of rilematovir for the manufacture of a medicament for the treatment or prophylaxis of a respiratory syncytial virus (RSV) infection in a patient. Additionally, or alternatively, provided herein is the use of a pharmaceutical composition of the invention comprising a hemi (L)-tartrate form of rilematovir for the manufacture of a medicament for the treatment of a patient suffering from moderate to severe infection by respiratory syncytial virus (RSV). In a further aspect, the hemi (L)-tartrate form of rilematovir is selected from the group consisting of polymorph Form 1, Form 2 and Form 3, and mixtures thereof, such as a mixture of polymorph Form 1 and Form 3.

In an embodiment the present invention provides a method of treating a respiratory syncytial virus (RSV) infection in a patient in need thereof comprising administering to the patient a pharmaceutical composition of the present invention comprising a therapeutically effective amount of the hemi (L)-tartrate form of rilematovir. Additionally, or alternatively, provided herein is a method of treating a patient suffering from moderate to severe infection by respiratory syncytial virus (RSV) comprising administering to the patient a pharmaceutical composition of the present invention comprising a therapeutically effective amount of the hemi (L)-tartrate form of rilematovir. In a further aspect, the hemi (L)-tartrate form of rilematovir is selected from the group consisting of polymorph Form 1, Form 2 and Form 3, and mixtures thereof, such as a mixture of polymorph Form 1 and Form 3. The patient may have one or more symptoms of an RSV infection. The respiratory syncytial virus may be RSV Type A. The respiratory syncytial virus may be RSV Type B.

Also provided are methods of ameliorating one or more symptoms of an RSV infection in a patient in need thereof comprising administering to the patient a pharmaceutical composition of the present invention comprising a prophylactically effective amount of a hemi (L)-tartrate form of rilematovir. The symptoms may be one or more of: congested or stuffy nose, sore or painful throat, trouble breathing, chest tightness, coughing, coughing up mucus or phlegm, feeling of weakness or fatigue. The patient may have a lower respiratory tract infection. Additionally, or alternatively, the patient may have bronchiolitis, pneumonia, or croup. The patient may have been diagnosed with an RSV infection. The respiratory syncytial virus may be RSV Type A. The respiratory syncytial virus may be RSV Type B. The RSV infection may have been confirmed by a laboratory test. Additionally, or alternatively, the method may further comprise obtaining the results of an RSV detecting laboratory test. The laboratory test may comprise detecting RSV in a nasal sample.

Also provided are methods of preventing an RSV infection in an individual at risk of developing an RSV infection comprising administering to the individual a pharmaceutical composition of the present invention comprising a prophylactically effective amount of a hemi (L)-tartrate form of rilematovir. The individual may be between 0 and about 5 years of age. The individual may be born prematurely. Additionally, or alternatively, the individual is an adult. Additionally, or alternatively, the individual is immunocompromised such as e.g. a hematopoietic stem cell transplant (HSCT) recipient.

Rilematovir is in phase III clinicals trials (ClinicalTrials.gov identifier: NCT04583280 and EudraCT Number: 2020-002023-11) to evaluate its efficacy and safety in hospitalized infants and children (greater than or equal to 28 days to less than or equal to 5 years) and, subsequent to completion of the neonatal substudy, in hospitalized neonates (born at term, less than 28 days of age) who are hospitalized with acute respiratory tract infection due to respiratory syncytial virus (RSV). Participants to the trial have an acute respiratory illness with at least one of the signs/symptoms listed in each of the following categories a), b) and c): a) an upper respiratory tract infection such as nasal congestion or rhinorrhea; and b) a lower respiratory tract infection such as increased respiratory effort (as evidenced by subcostal, intercostal or tracheosternal retractions, grunting, head bobbing, nasal flaring, or tachypnea), wheezing, cough (cough cannot be the only lower respiratory tract infection (LRTI) sign/symptom present, i.e. another LRTI sign/symptom needs to be present for eligibility), cyanosis, or apnea; and c) systemic/general symptoms such as feeding difficulties (defined as <75% intake of normal food amounts); dehydration; fever; disturbed sleep, or disturbed activity level (irritable/restless/agitated/less responsive).

Immunocompromised individuals (e.g. hematopoietic stem cell transplant (HSCT) recipients, solid organ transplant recipients, HIV-infected patients) have a reduced ability to combat infection due to an impaired or weakened immune system. Within the immunocompromised population, HSCT recipients are generally regarded as having a particularly high risk for more severe disease caused by RSV, representing a substantial unmet need for antiviral treatment of RSV infections in this participant population. The progression of RSV from an URTI (upper respiratory tract infection such as e.g. nasal congestion, rhinorrhea, pharyngitis, cough, and/or worsening of one of these chronic (associated with previously existing diagnosis, example, chronic rhinorrhea, seasonal allergies, chronic lung disease) respiratory symptoms) to a LRTI (lower respiratory tract infection) can cause significant morbidity, often leading to hospitalization, intensive care unit admission for supportive care and may furthermore result in mortality in RSV infected HSCT recipients. Accordingly a method is provided to treat or prevent RSV lower tract respiratory infections (LRTI's) in HSCT recipients with a RSV upper respiratory tract infection (URTI) comprising administering to the HSCT recipient a pharmaceutical composition of the present invention comprising a prophylactically or therapeutically effective amount of a hemi (L)-tartrate form of rilematovir. Also provided is a pharmaceutical composition comprising a hemi (L)-tartrate form of rilematovir for use in the treatment or prevention of RSV lower tract respiratory infections (LRTI's) in HSCT recipients with a RSV upper respiratory tract infection (URTI). The hemi (L)-tartrate form of rilematovir is selected from the group consisting of polymorph Form 1, Form 2 and Form 3, and mixtures thereof, such as a mixture of polymorph Form 1 and Form 3.

As used herein, "treatment" or "treating" is an approach for obtaining beneficial or desired results including clinical results. For example, beneficial or desired results in treating a viral infection include, but are not limited to, one or more of the following: eliminating or lessening the severity of one or more symptoms resulting from the viral infection (such as but not limited to coughing, sneezing, runny nose, sore throat, fever, decrease of appetite, irritability, decreased activity, apnea, and wheezing), increasing the quality of life of those suffering from the viral infection, decreasing the dose of other medications required to treat the viral infection, delaying the progression of the viral infection, and/or prolonging survival of an individual.

As used herein, "preventing" a viral infection is an approach for eliminating or reducing the risk of developing a viral infection or delaying the onset of a viral infection, including biochemical, histological and/or behavioral symptoms of a viral infection. Prevention may be in the context of an individual at risk of developing the viral infection, such as where the "at risk" individual does not develop viral infection over a period of time, such as during a viral season or during a period of exposure to the virus, which may be days to weeks to months. An individual "at risk" of developing a viral infection is an individual with one or more risk factors for developing the viral infection but who has not been diagnosed with and does not display symptoms consistent with a viral infection. Risk factors for developing an RSV infection include but are not limited to an individual's age (young children under age 5 such as children between about 0 and about 2 years of age, including infants, and individuals greater than 65 years of age), premature birth, co-morbidities associated with RSV and individuals who are immuno-compromised.

As used herein, a "therapeutically effective amount" or a "therapeutically effective dosage" of a hemi (L)-tartrate form of rilematovir or a pharmaceutical composition comprising a hemi (L)-tartrate form of rilematovir is an amount sufficient to produce a desired therapeutic outcome. A therapeutically effective amount or a therapeutically effective dosage can be administered in one or more administrations per day. A therapeutically effective amount or dosage may be considered in the context of administering one or more therapeutic agents (e.g., a compound, or pharmaceutically acceptable salt thereof), and a single agent may be considered to be given in a therapeutically effective amount if, in conjunction with one or more other agents, a desired therapeutic outcome is achieved. Suitable doses of any of the co-administered compounds may optionally be lowered due to the combined action (e.g., additive or synergistic effects) of the compounds.

As used herein, a "prophylactically effective amount" or "prophylactically effective dosage" is an amount sufficient to effect the preventative result of eliminating or reducing the risk of developing a viral infection or delaying the onset of a viral infection, including biochemical, histological and/or behavioral symptoms of a viral infection. A prophylactically effective amount or a prophylactically effective dosage can be administered in one or more administrations per day and over a period of time in which such prevention is desired. Additionally, the present invention provides pharmaceutical compositions comprising at least one pharmaceutically acceptable carrier and a therapeutically effective amount of hemi (L)-tartrate form of rilematovir.

"Dosage" or "dosage" may mean either a single administration of a composition or can mean several administrations of the same composition depending on context. For example if the composition is given twice a day, a dose could be taken to mean two administrations of the same composition, in suitably measured amounts. Thus the same "dose" may be given two or three times (or more if necessary) in the treatment regimen before progressing to the subsequent dose, which would be of a composition having a different given amount of medication. However as defined above a unit dose means a single dose given a single time, i.e. in one administration.

"Patient" may be any human treated with a composition of this invention. The patient is preferably a human child but could also be an adult.

The dosage will depend on the age, weight, condition and disease of the patient. These amounts may be determined by a skilled person with routine experimentation. For pediatric use, the dosage depends upon the age and the weight of the patient and can be from 2.5 mg/kg to 10 mg/kg per day. Dosing can be done once daily (QD) or twice daily (BID). In particular for pediatric use when dosing twice a day (BID) is given, the dosing can be 2.5 mg/kg BID for children of 1 month old up to 3 months old, 3 mg/kg BID for children of 3 months old up to 6 months old, or 4.5 mg/kg BID for children of 6 months old up to 36 months old (based on the amount of rilematovir). Dosing is typically done for a period of seven days.

For adults, the dosing can be once daily (QD) or twice daily (BID) and can be 100 mg, 125 mg, 150 mg, 200 mg, 250 mg, 300 mg, 350 mg, 400 mg, 500 mg, or 600 mg (total amount per day based on the amount of rilematovir). A particular dosing is 250 mg twice daily (BID). Dosing is typically done for a period of seven days.

For HSCT recipients the dosing is 250 mg of rilematovir twice daily (bid) for 21 days (without coadministration with moderate or strong CYP3A4 inhibitors), or 125 mg of rilematovir twice daily (bid) for 21 days when co-administered with moderate or strong CYP3A4 inhibitors (with the exception of posaconazole), or 125 mg once daily (QD) for 21 days (when coadministered with posaconazole).

Example 1: Hemi (L)-Tartrate Form of Rilematovir (Polymorph Form 1)

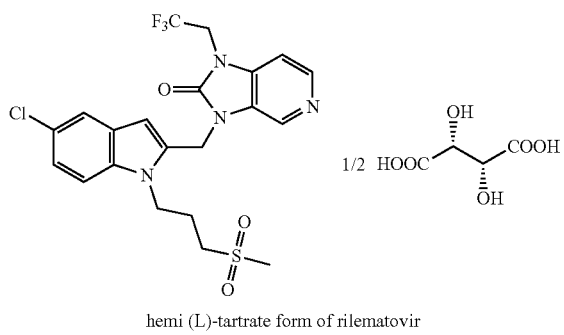 [SMILES: CS(=O)(=O)CCCn1c(Cn2c(=O)n(CC(F)(F)F)c3ccncc32)cc2cc(Cl)ccc21 ; O=C(O)[C@H](O)[C@@H](O)C(=O)O]

hemi (L)-tartrate form of rilematovir

Rilematovir (30.4 g) and L-tartaric acid (4.3 g) were dissolved in MEK (methylethylketone) (1520 mL) at a temperature of 75-77° C., the mixture was cooled to 67° C. and seeding material was added. The mixture was gradually cooled to 5° C. The slurry was filtered and the residue was washed with cold MEK and dried under reduced pressure to obtain the hemi (L)-tartrate form of rilematovir (28.0 g, 80% yield).

Polymorph Form 1 was also obtained when the crystallisation procedure was performed in the following solvents: acetone, acetonitrile, 2-propanol, or THF.

Seeding material was obtained by spontaneous crystallization (heating/cooling) from MEK.

$^1$H NMR (500 MHz, DMSO-$d_6$) δ ppm 1.96 (quin J=7.70 Hz, 2H) 2.98 (s, 3H) 3.16 (m, 2H) 4.29 (s, 1H) 4.39 (br t J=7.60 Hz, 2H) 4.90 (q, J=9.10 Hz, 2H) 5.41 (s, 2H) 6.48 (s, 1H) 7.17 (dd J=8.70, 2.00 Hz, 1H) 7.44 (d J=5.10 Hz, 1H) 7.55 (d J=8.70 Hz, 1H) 7.57 (d, J=1.80 Hz, 1H) 8.31 (d, J=5.30 Hz, 1H) 8.49 (s, 1H) 12.62 (bs, 1H)

$^{13}$C NMR (125 MHz, DMSO-$d_6$) δ ppm 22.90 37.50 40.17 41.56 41.80 (q, J=31.6 Hz) 50.79 72.07 101.85 104.51 111.50 119.50 121.63 124.25 124.27 (q: J=277.9 Hz) 126.15 128.00 129.91 134.94 135.24 135.53 143.19 152.39 173.10

Melting point (DSC): 206° C. (with decomposition).

Example 2: Hemi (L)-Tartrate Form of Rilematovir (Polymorph Form 2)

The polymorph Form 2 of the hemi (L)-tartrate form of rilematovir was prepared by heating the polymorph Form 1 in cyclohexanone up to a temperature of 85° C. at a heating rate of 10° C./min and keeping it isothermal for 5 minutes. After cooling to room temperature, the crystalline Form 2 hemi (L)-tartrate form of rilematovir was isolated by filtration.

Example 3: Long Term Storage of Aqueous Suspension

A liquid aqueous suspension comprising Form 1 of the hemi (L)-tartrate form of rilematovir as described in Examples 10, 11, 14 or 15 was stored in a sealed glass vial at a temperature of 30° C., 40° C., and 50° C. Over a period of 8 months samples were taken and analysed (e.g. by XPRD or solid state $^{19}$F-NMR spectroscopy). No free form of rilematovir was observed thereby indicating that in an aqueous suspension the hemi (L)-tartrate form of rilematovir does not disproportionate.

It was also observed using XPRD and solid state $^{19}$F-NMR spectroscopy that over time Form 1 converts into Form 3. FIG. 6 is the solid state $^{19}$F-NMR spectrum of Form 1 having peaks at −70.004 ppm and −73.248 ppm. FIG. 7 is the solid state $^{19}$F-NMR spectrum of Form 3 having a peak at −70.122 ppm.

Example 4: Solubility of Rilematovir and Hemi (L)-Tartrate Form of Rilematovir

Determination of the equilibrium solubility of rilematovir in its free base form and its hemi (L)-tartrate form in fed state human intestinal fluids.

The thermodynamic solubility of rilematovir and the hemi (L)-tartrate form of rilematovir was determined using human intestinal fluids obtained from human volunteers in fed state. The pools of human intestinal fluids were prepared from individual intestinal aspirates collected among healthy volunteers under fed state conditions. Fed HR (high responders) pools were build up from duodenal samples in the fed state from volunteers with a clear postprandial bile salt increase.

An excess of test compound (2.1-2.6 mg) was weighed of in 500 μl Eppendorf tubes. A small magnetic stirrer bar (about 5 mm in length) and 300 μl of the respective human intestinal fluids at 37° C. were added to the Eppendorf tubes containing an excess of test compound. The mixtures were vortexed for a few seconds and placed on a magnetic stirrer plate (100 rpm) at 37° C.

After 24 hours, the Eppendorf tubes were centrifuged for 5 minutes at 12000 rpm (to separate dissolved from non-dissolved material). 10p1 of the supernatant was diluted into 100 μl methanol), well mixed and centrifuged for 1 minute to separate precipitated protein fraction. The test compound was quantified in the resulting supernatant using UPLC-UV quantification.

The pH was measured at the end of the experiment for each condition ($pH_{end}$ in Table 1).

TABLE 1 solubility for rilematovir (crystalline free base form) and hemi (L)-tartrate form of rilematovir (hemi tartrate form)

| Media | Test compound | $pH_{end}$ | Conc (μg/mL) | Average (μg/mL) | Stdev (μg/mL) |
|---|---|---|---|---|---|
| Fed HR pool | free base | 6.2 | 33.96 | 34.42 | 2.19 |
| Fed HR pool | free base | 6.2 | 36.80 | | |
| Fed HR pool | free base | 6.7 | 32.50 | | |
| Fed HR pool | hemi tartrate form | 6.0 | 102.07 | 117.31 | 13.35 |
| Fed HR pool | hemi tartrate form | 6.0 | 122.93 | | |
| Fed HR pool | hemi tartrate form | 6.0 | 126.92 | | |

Conclusion: solubility of the hemi (L)-tartrate form of rilematovir in fed state human intestinal fluids is more than three times higher than the free base form of rilematovir.

Example 5: Kinetic Solubility of Rilematovir and Hemi (L)-Tartrate Form of Rilematovir (Polymorph Form 1) in Biorelevant Media Comprising HPMC The kinetic solubility of rilematovir and the hemi (L)-tartrate form of rilematovir in different biorelevant medium (FaSSIF and FeSSIF) in the presence or absence of HPMC E5 was analysed.

Materials
  rilematovir (crystalline free base form)
  hemi (L)-tartrate form of rilematovir (polymorph Form 1)—(hemi tartrate form)
  HPMC 2910 5 MPa·s
  FaSSIF: Fasted State Simulated Intestinal Fluid
  FeSSIF: Fed State Simulated Intestinal Fluid Method An excess amount of rilematovir or the hemi (L)-tartrate form of rilematovir was added to biorelevant medium (approximately 5 mg solid/mL medium was used). For solubility measurements in the presence of HPMC, HMPC was dissolved in the biorelevant medium at a concentration of 1.39 mg/mL.

The media were stirred at 150 rpm at a temperature of 37° C. Time-dependent measurements were performed by removing 10 mL aliquots after 30 minutes, 1 hour and 2 hours. Undissolved solid material in the aliquot was removed using a Whatman SPARTAN RC syringe filter (diameter: 30 mm; pore size: 0.2 µm). Afterwards, a suitable dilution was made in NMP/water 30/70; v/v to avoid precipitation. The concentration of rilematovir, or the hemi (L)-tartrate form of rilematovir, in solution was determined using UPLC-UV.

Solubility Results

The summary of the kinetic solubility in different biorelevant media at 37° C. with and without HPMC E5 is shown in Table 2 and Table 3.

TABLE 2 kinetic solubility of rilematovir in different biorelevant media with and without HPMC E5 at 37° C. The concentrations are expressed as µg rilematovir/mL.

| Medium | HPMC E5 (mg/mL) | 30 minutes concentration of free base (µg/mL) | 60 minutes concentration of free base (µg/mL) | 120 minutes concentration of free base (µg/mL) |
|---|---|---|---|---|
| FaSSIF pH 6.5 | / | 1.1 | 1.1 | 1.2 |
| FaSSIF pH 6.5 | 1.39 | 1.2 | 1.3 | 1.5 |
| FeSSIF pH 5.0 | / | 12.5 | 13.2 | 13.7 |
| FeSSIF pH 5.0 | 1.39 | 12.3 | 13.4 | 13.9 |

TABLE 3 kinetic solubility of hemi (L)-tartrate form of rilematovir (polymorph Form 1) in different biorelevant media with and without HPMC E5 at 37° C. The concentrations of the hemi tartrate form are expressed as µg rilematovir/mL to allow for a direct comparison in kinetic solubility.

| Medium | HPMC E5 (mg/mL) | 30 minutes concentration of hemi tartrate (µg/mL) | 60 minutes concentration of hemi tartrate (µg/mL) | 120 minutes concentration of hemi tartrate (µg/mL) |
|---|---|---|---|---|
| FaSSIF pH 6.5 | / | 4.4 | 3.4 | 3.0 |
| FaSSIF pH 6.5 | 1.39 | 107.7 | 93.1 | 75.9 |
| FeSSIF pH 5.0 | / | 82.8 | 67.1 | 58.6 |
| FeSSIF pH 5.0 | 1.39 | 1011.3 | 853.1 | 689.0 |

Conclusion: the kinetic solubility of the hemi (L)-tartrate form of rilematovir is three (in FaSSIF) to six (in FeSSIF) times higher in biorelevant media in the absence of the suspending agent HPMC. In the presence of the suspending agent HPMC, the kinetic solubility of the hemi (L)-tartrate form of rilematovir is 50 to more than 80 times higher in biorelevant media.

Example 6: Intrinsic Dissolution Rate of Rilematovir and Hemi (L)-Tartrate Form of Rilematovir (Polymorph Form 1)

Intrinsic Dissolution Method Parameters:

| Apparatus | µDISS Profiler ™ |
|---|---|
| Stirrer speed | 100 rpm |
| Medium | 0.01N HCl Blank FaSSIf-FaSSIF |
| Volume | 20 mL |
| Temperature | 37.0 ± 0.5° C. |
| Pathlenght fiber optic | 5 mm |
| Analytical Method for 0.01N HCl and Blank FaSSIF | UV detection at 278 nm with baseline correction at 380 nm |
| Analytical Method for FaSSIF | $2^{nd}$ derivative between the range of UV detection at 306 nm to 324 nm |

FaSSIF: Fasted State Simulated Intestinal Fluid
Blank FaSSIF: FaSSIF without presence of bile components Pellet Compression Parameters

| Apparatus: | Mini-IDR compression system |
|---|---|
| Amount of drug substance: | 5 mg of pure drug substance |
| Compression: | 40 bar for 1 minute |
| Pellet Area: | 0.0754 cm² |

TABLE 4 intrinsic dissolution rate (IDR) for rilematovir (crystalline free base form) and hemi (L)-tartrate form of rilematovir (hemi tartrate form)

| Test compound | Medium: 0.01N HCl IDR (μg/min/cm²) | Medium: Blank FaSSIF IDR (μg/min/cm²) | Medium: FASSIF IDR (μg/min/cm²) |
|---|---|---|---|
| free base | 8.98 | 3.06 | <1 |
| hemi tartrate form | 147 | 5.45 | 2.10 |

Conclusion: intrinsic dissolution rate (IDR) of of the hemi (L)-tartrate form of rilematovir in three biorelevant media is higher than the free base form of rilematovir.

Example 7: XRPD Data for Hemi (L)-Tartrate Form of Rilematovir—Polymorph Form 1

Measurement Conditions:
X-ray power diffraction (XRPD) analysis was carried out on a PANalytical (Philips) X'PertPRO MPD diffractometer. The instrument is equipped with a CI LFF X-ray tube. The compound was filled in a 16 mm cavity holder.

| | XRD measurement |
|---|---|
| Raw Data Origin | (*.XRDML) |
| Scan Axis | Gonio |
| Start Position [°2Th.] | 3.0160 |
| End Position [°2Th.] | 49.9870 |
| Step Size [°2Th.] | 0.0170 |
| Scan Step Time [s] | 30.3630 |
| Scan Type | Continuous |
| Offset [°2Th.] | 0.0000 |
| Divergence Slit Type | Automatic |
| Irradiated Length [mm] | 10.00 |
| Specimen Length [mm] | 10.00 |
| Receiving Slit Size [mm] | 0.1000 |
| Measurement Temperature [° C.] | 25.00 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 |
| Generator Settings | 40 mA, 45 kV |
| Diffractometer Number | 0 |
| Goniometer Radius [mm] | 240.00 |
| Dist. Focus-Diverg. Slit [mm] | 91.00 |
| Incident Beam Monochromator | No |
| Spinning | No |

Peak List 1:

| Pos. [°2Th.] | Height [cts] | FWHM Left [°2Th.] | d-spacing [Å] | Rel. Int. [%] |
|---|---|---|---|---|
| 3.1161 | 1766.25 | 0.0836 | 28.35383 | 13.81 |
| 4.9584 | 183.34 | 0.1004 | 17.82230 | 1.43 |
| 5.8684 | 616.42 | 0.0669 | 15.06065 | 4.82 |
| 7.9249 | 2462.70 | 0.1004 | 11.15645 | 19.26 |
| 9.2885 | 330.91 | 0.0836 | 9.52139 | 2.59 |
| 9.9262 | 391.13 | 0.0836 | 8.91113 | 3.06 |
| 10.5350 | 549.21 | 0.1004 | 8.39746 | 4.30 |
| 12.3922 | 3581.83 | 0.1171 | 7.14284 | 28.01 |
| 13.5398 | 1372.72 | 0.1506 | 6.53989 | 10.74 |
| 14.8937 | 347.27 | 0.1338 | 5.94828 | 2.72 |
| 15.4920 | 1619.51 | 0.1004 | 5.71989 | 12.67 |
| 15.8178 | 3681.63 | 0.0836 | 5.60280 | 28.80 |
| 16.1935 | 12785.50 | 0.1840 | 5.47365 | 100.00 |
| 17.9950 | 3837.19 | 0.1171 | 4.92954 | 30.01 |
| 18.4696 | 2387.67 | 0.3680 | 4.80393 | 18.67 |
| 19.2851 | 3036.96 | 0.1171 | 4.60259 | 23.75 |
| 19.4982 | 1156.30 | 0.0669 | 4.55275 | 9.04 |
| 20.1817 | 3747.91 | 0.1673 | 4.40008 | 29.31 |
| 20.7670 | 1217.91 | 0.1338 | 4.27738 | 9.53 |
| 21.1457 | 407.57 | 0.1171 | 4.20162 | 3.19 |
| 21.5746 | 2183.64 | 0.1506 | 4.11906 | 17.08 |
| 21.9356 | 2223.53 | 0.1673 | 4.05207 | 17.39 |
| 22.2972 | 2934.44 | 0.1673 | 3.98717 | 22.95 |
| 22.7196 | 5610.45 | 0.1840 | 3.91400 | 43.88 |
| 23.4064 | 1772.97 | 0.1338 | 3.80068 | 13.87 |
| 24.1665 | 3136.92 | 0.1506 | 3.68283 | 24.53 |
| 24.8965 | 722.22 | 0.1338 | 3.57647 | 5.65 |
| 25.8284 | 1453.54 | 0.2007 | 3.44951 | 11.37 |
| 26.7448 | 4814.57 | 0.2342 | 3.33336 | 37.66 |
| 27.9191 | 3284.45 | 0.1840 | 3.19576 | 25.69 |
| 28.4861 | 1038.83 | 0.1004 | 3.13343 | 8.13 |
| 29.3024 | 291.68 | 0.3346 | 3.04798 | 2.28 |
| 30.1133 | 478.00 | 0.2007 | 2.96772 | 3.74 |
| 30.6606 | 326.85 | 0.2007 | 2.91598 | 2.56 |
| 31.2760 | 1087.83 | 0.3011 | 2.85999 | 8.51 |
| 32.3385 | 287.67 | 0.2007 | 2.76841 | 2.25 |
| 33.9147 | 1091.69 | 0.3346 | 2.64327 | 8.54 |
| 35.0292 | 414.62 | 0.2342 | 2.56169 | 3.24 |
| 36.0499 | 600.68 | 0.4015 | 2.49147 | 4.70 |
| 37.0212 | 505.93 | 0.2342 | 2.42830 | 3.96 |
| 37.6771 | 316.32 | 0.2676 | 2.38752 | 2.47 |
| 39.5850 | 289.02 | 0.2007 | 2.27674 | 2.26 |
| 40.4589 | 258.50 | 0.2676 | 2.22955 | 2.02 |
| 41.6730 | 215.66 | 0.2676 | 2.16736 | 1.69 |
| 42.2138 | 147.31 | 0.2007 | 2.14084 | 1.15 |
| 43.9086 | 164.92 | 0.2007 | 2.06206 | 1.29 |
| 44.9118 | 251.98 | 0.2676 | 2.01831 | 1.97 |
| 46.0213 | 715.45 | 0.1673 | 1.97220 | 5.60 |
| 47.8850 | 293.46 | 0.3346 | 1.89971 | 2.30 |
| 49.1856 | 137.79 | 0.4015 | 1.85247 | 1.08 |

| Unit cell parameters | Polymorph Form 1 |
|---|---|
| Space group | P 1 |
| a (Å) | 5.0536 |
| b (Å) | 28.588 |
| c (Å) | 17.844 |
| α (°) | 90.341 |
| β (°) | 86.981 |
| γ (°) | 90.351 |
| Cell volume (Å³) | 2574 |
| Rwp (%) | 4.12 |

Example 8: XRPD Data for Hemi (L)-Tartrate Form of Rilematovir—Polymorph Form 2

Measurement Conditions:

| | XRD measurement |
|---|---|
| Raw Data Origin | (*.XRDML) |
| Scan Axis | Gonio |
| Start Position [°2Th.] | 3.0164 |
| End Position [°2Th.] | 49.9874 |
| Step Size [°2Th.] | 0.0170 |
| Scan Step Time [s] | 29.8450 |
| Scan Type | Continuous |
| PSD Mode | Scanning |

-continued

| Raw Data Origin | XRD measurement (*.XRDML) |
|---|---|
| PSD Length [°2Th.] | 2.12 |
| Offset [°2Th.] | 0.0000 |
| Divergence Slit Type | Automatic |
| Irradiated Length [mm] | 15.00 |
| Specimen Length [mm] | 10.00 |
| Measurement Temperature [° C.] | 25.00 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 |
| Generator Settings | 40 mA, 45 kV |
| Diffractometer Type | 0000000000002547 |
| Diffractometer Number | 0 |
| Goniometer Radius [mm] | 240.00 |
| Dist. Focus-Diverg. Slit [mm] | 100.00 |
| Incident Beam Monochromator | No |
| Spinning | Yes. |

Peak list 2:

| Pos. [°2Th.] | Height [cts] | FWHM Left [°2Th.] | d-spacing [Å] | Rel. Int. [%] |
|---|---|---|---|---|
| 5.1997 | 526.25 | 0.3011 | 16.99567 | 14.49 |
| 7.0883 | 885.20 | 0.2676 | 12.47108 | 24.38 |
| 8.3901 | 261.55 | 0.6691 | 10.53886 | 7.20 |
| 11.8698 | 348.19 | 0.2676 | 7.45596 | 9.59 |
| 12.9354 | 201.90 | 0.4684 | 6.84406 | 5.56 |
| 14.0773 | 2247.08 | 0.0836 | 6.29137 | 61.88 |
| 14.4108 | 3607.09 | 0.2342 | 6.14650 | 99.33 |
| 14.7320 | 2622.71 | 0.0836 | 6.01320 | 72.22 |
| 15.5639 | 772.50 | 0.1673 | 5.69362 | 21.27 |
| 16.4487 | 3557.78 | 0.1506 | 5.38929 | 97.97 |
| 17.1140 | 3042.33 | 0.1171 | 5.18126 | 83.78 |
| 18.4110 | 2002.66 | 0.4684 | 4.81909 | 55.15 |
| 19.0482 | 3631.38 | 0.1338 | 4.65930 | 100.00 |
| 19.3859 | 2927.17 | 0.2676 | 4.57888 | 80.61 |
| 20.7282 | 2743.73 | 0.2007 | 4.28529 | 75.56 |
| 21.6521 | 2087.64 | 0.1673 | 4.10450 | 57.49 |
| 22.6146 | 2398.84 | 0.4349 | 3.93192 | 66.06 |
| 23.4914 | 1603.36 | 0.3011 | 3.78712 | 44.15 |
| 24.0322 | 1024.53 | 0.2007 | 3.70311 | 28.21 |
| 24.7579 | 1204.45 | 0.2676 | 3.59618 | 33.17 |
| 25.5504 | 728.55 | 0.3011 | 3.48640 | 20.06 |
| 26.3319 | 553.40 | 0.2007 | 3.38469 | 15.24 |
| 26.9061 | 1272.32 | 0.2007 | 3.31374 | 35.04 |
| 27.2515 | 1583.93 | 0.2007 | 3.27253 | 43.62 |
| 27.8321 | 1545.37 | 0.3346 | 3.20556 | 42.56 |
| 28.7780 | 1369.55 | 0.1171 | 3.10232 | 37.71 |
| 29.4114 | 892.80 | 0.2676 | 3.03693 | 24.59 |
| 29.9359 | 418.78 | 0.2676 | 2.98490 | 11.53 |
| 30.9369 | 212.38 | 0.2676 | 2.89057 | 5.85 |
| 31.6431 | 362.77 | 0.2342 | 2.82765 | 9.99 |
| 32.3396 | 293.80 | 0.2342 | 2.76833 | 8.09 |
| 32.9649 | 220.64 | 0.3346 | 2.71723 | 6.08 |
| 33.7587 | 207.71 | 0.2676 | 2.65513 | 5.72 |
| 34.4558 | 214.60 | 0.2676 | 2.60300 | 5.91 |
| 35.1181 | 122.74 | 0.2676 | 2.55541 | 3.38 |
| 37.0118 | 195.18 | 0.4684 | 2.42890 | 5.37 |
| 37.7650 | 250.29 | 0.2007 | 2.38217 | 6.89 |
| 39.7028 | 144.82 | 0.4015 | 2.27026 | 3.99 |
| 43.9318 | 119.03 | 0.5353 | 2.06103 | 3.28 |
| 46.4674 | 190.23 | 0.5353 | 1.95430 | 5.24 |
| 47.3930 | 129.18 | 0.4015 | 1.91827 | 3.56 |

Example 9: XRPD Data for Hemi (L)-Tartrate Form of Rilematovir—Polymorph Form 3

Form 3 was obtained from the samples isolated in the experiments of Example 3.

Measurement Conditions:

| Raw Data Origin | XRD measurement (*.XRDML) |
|---|---|
| Scan Axis | Gonio |
| Start Position [°2Th.] | 3.0080 |
| End Position [°2Th.] | 49.9790 |
| Step Size [°2Th.] | 0.0170 |
| Scan Step Time [s] | 30.3630 |
| Scan Type | Continuous |
| Offset [°2Th.] | 0.0000 |
| Divergence Slit Type | Automatic |
| Irradiated Length [mm] | 15.00 |
| Specimen Length [mm] | 10.00 |
| Receiving Slit Size [mm] | 0.1000 |
| Measurement Temperature [° C.] | 25.00 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 |
| Generator Settings | 40 mA, 45 kV |
| Diffractometer Number | 0 |
| Goniometer Radius [mm] | 240.00 |
| Dist. Focus-Diverg. Slit [mm] | 91.00 |
| Incident Beam Monochromator | No |
| Spinning | No. |

Peak list 3:

| Pos. [°2Th.] | Height [cts] | FWHM Left [°2Th.] | d-spacing [Å] | Rel. Int. [%] |
|---|---|---|---|---|
| 3.1744 | 262.32 | 0.1004 | 27.83337 | 3.26 |
| 5.7782 | 125.86 | 0.2007 | 15.29543 | 1.56 |
| 7.7190 | 689.44 | 0.1004 | 11.45352 | 8.56 |
| 8.2159 | 459.27 | 0.1338 | 10.76193 | 5.70 |
| 9.1788 | 140.85 | 0.2007 | 9.63497 | 1.75 |
| 10.2719 | 164.18 | 0.1673 | 8.61195 | 2.04 |
| 12.2183 | 4209.03 | 0.1506 | 7.24411 | 52.26 |
| 12.3725 | 2360.61 | 0.1004 | 7.15413 | 29.31 |
| 13.6155 | 212.59 | 0.2007 | 6.50370 | 2.64 |
| 14.2408 | 794.51 | 0.1171 | 6.21948 | 9.86 |
| 15.2742 | 4210.35 | 0.1004 | 5.80095 | 52.28 |
| 15.4543 | 4072.06 | 0.1004 | 5.73377 | 50.56 |
| 16.1960 | 5238.70 | 0.1004 | 5.47282 | 65.05 |
| 16.4716 | 8053.95 | 0.1840 | 5.38187 | 100.00 |
| 16.9654 | 1587.92 | 0.1171 | 5.22630 | 19.72 |
| 17.4438 | 775.23 | 0.1673 | 5.08405 | 9.63 |
| 17.9289 | 492.25 | 0.1673 | 4.94756 | 6.11 |
| 18.7715 | 6035.47 | 0.1673 | 4.72733 | 74.94 |
| 19.4458 | 430.12 | 0.1004 | 4.56491 | 5.34 |
| 19.8520 | 457.93 | 0.1506 | 4.47242 | 5.69 |
| 20.3905 | 1208.38 | 0.1004 | 4.35550 | 15.00 |
| 20.6484 | 2138.53 | 0.1004 | 4.30167 | 26.55 |
| 21.3386 | 578.84 | 0.2007 | 4.16408 | 7.19 |
| 21.7906 | 2260.51 | 0.1171 | 4.07871 | 28.07 |
| 22.5357 | 828.05 | 0.2007 | 3.94551 | 10.28 |
| 23.1558 | 1623.35 | 0.1004 | 3.84124 | 20.16 |
| 24.6308 | 4216.76 | 0.1338 | 3.61445 | 52.36 |
| 25.7180 | 386.76 | 0.1171 | 3.46407 | 4.80 |
| 26.1421 | 1089.86 | 0.1506 | 3.40882 | 13.53 |
| 26.9241 | 1013.79 | 0.2007 | 3.31157 | 12.59 |
| 27.3933 | 1525.11 | 0.1338 | 3.25590 | 18.94 |
| 27.8998 | 959.80 | 0.1171 | 3.19793 | 11.92 |
| 28.5956 | 1840.82 | 0.1171 | 3.12168 | 22.86 |
| 31.0334 | 1082.88 | 0.2007 | 2.88180 | 13.45 |
| 31.7314 | 293.18 | 0.1673 | 2.81998 | 3.64 |
| 32.2387 | 60.21 | 0.2342 | 2.77676 | 0.75 |
| 32.8430 | 803.01 | 0.2342 | 2.72704 | 9.97 |

-continued

| Pos. [°2Th.] | Height [cts] | FWHM Left [°2Th.] | d-spacing [Å] | Rel. Int. [%] |
|---|---|---|---|---|
| 34.1773 | 853.12 | 0.2007 | 2.62356 | 10.59 |
| 34.8694 | 234.53 | 0.2676 | 2.57306 | 2.91 |
| 35.7466 | 749.06 | 0.2676 | 2.51191 | 9.30 |
| 36.7198 | 299.26 | 0.2007 | 2.44754 | 3.72 |
| 37.4889 | 142.84 | 0.3346 | 2.39908 | 1.77 |
| 38.7074 | 377.95 | 0.2007 | 2.32631 | 4.69 |
| 39.4901 | 253.28 | 0.2007 | 2.28199 | 3.14 |
| 40.7864 | 198.49 | 0.2007 | 2.21241 | 2.46 |
| 41.3781 | 466.27 | 0.2342 | 2.18213 | 5.79 |
| 42.9570 | 242.62 | 0.4015 | 2.10551 | 3.01 |
| 43.9196 | 255.91 | 0.2342 | 2.06157 | 3.18 |
| 44.5843 | 239.97 | 0.4015 | 2.03237 | 2.98 |
| 45.7792 | 162.86 | 0.2342 | 1.98206 | 2.02 |

| Unit cell parameters | Form 3 |
|---|---|
| Space group | P 1 |
| a (Å) | 5.030 |
| b (Å) | 28.934 |
| c (Å) | 17.313 |
| α (°) | 93.712 |
| β (°) | 85.085 |
| γ (°) | 90.657 |
| Cell volume (Å$^3$) | 2505 |
| Rwp (%) | 2.44 |

Example 10: Liquid Aqueous Suspension Suitable for Pediatric Use

A 100 mL suspension having the composition given in the table below was prepared.

| Ingredient | Amount |
|---|---|
| hemi (L)-tartrate form of rilematovir | 2300 mg |
| (L)-tartaric acid | 750 mg |
| HPMC 2910 | 5000 mg |
| sodium methyl paraben | 114 mg |
| sodium ethyl paraben | 57 mg |
| sucralose | 500 mg |
| strawberry flavor | 100 mg |
| simethicone | 30 mg |
| NaOH | to adjust pH to 3.2 |
| purified water | to adjust to volume of 100 mL |

Water (80 mL) was transferred into a compounding vessel, simethicone was added and a high shear homogenizer was used to homogenize until a homogeneous emulsion was obtained. Then HPMC, sodium methyl paraben, sodium ethyl paraben, (L)-tartaric acid, sucralose, and strawberry flavor were added in succession, each time followed by mixing till the ingredient was dissolved. NaOH (5 M) was added to adjust the pH to 3.2. Hemi (L)-tartrate form of rilematovir was added while stirring and water was added to adjust the volume to 100 mL.

Example 11: Liquid Aqueous Suspension Suitable for Adult Use

A 100 mL suspension having the composition given in the table below was prepared.

| Ingredient | Amount |
|---|---|
| hemi (L)-tartrate form of rilematovir | 5750 mg |
| (L)-tartaric acid | 750 mg |
| HPMC 2910 | 5000 mg |
| sodium methyl paraben | 114 mg |
| sodium ethyl paraben | 57 mg |
| sucralose | 500 mg |
| strawberry flavor | 100 mg |
| simethicone | 30 mg |
| NaOH | to adjust pH to 3.2 |
| purified water | to adjust to volume of 1 mL |

Water (80 mL) was transferred into a compounding vessel, simethicone was added and a high shear homogenizer was used to homogenize until a homogeneous emulsion was obtained. Then HPMC, sodium methyl paraben, sodium ethyl paraben, (L)-tartaric acid, sucralose, and strawberry flavor were added in succession, each time followed by mixing till the ingredient was dissolved. NaOH (5 M) was added to adjust the pH to 3.2. Hemi (L)-tartrate form of rilematovir was added while stirring and water was added to adjust the volume to 100 mL.

Example 12: Pharmaceutical Product Suitable for Reconstitution

A first glass bottle filled with 9.2 g of a powder blend having the composition given in the table below was prepared.

| Ingredient | Amount |
|---|---|
| hemi (L)-tartrate form of rilematovir | 2.30 g |
| mannitol | 6.81 g |
| silicon dioxide | 92 mg |

A second glass bottle filled with 100 mL of a solution having the composition given in the table below was prepared.

| Ingredient | Amount |
|---|---|
| (L)-tartaric acid | 799.9 mg |
| HPMC 2910 | 5329 mg |
| sodium methyl paraben | 121.5 mg |
| sodium ethyl paraben | 60.2 mg |
| sucralose | 532.9 mg |
| strawberry flavor | 106.6 mg |
| simethicone | 31.98 mg |
| NaOH | to adjust pH to 3.2 |
| purified water | to adjust to volume of 100 mL |

Preparation

Water (80 mL) was transferred into a compounding vessel, simethicone was added and a high shear homogenizer was used to homogenize until a homogeneous emulsion was obtained. Then HPMC, sodium methyl paraben, sodium ethyl paraben, (L)-tartaric acid, sucralose, and strawberry flavor were added in succession, each time followed by mixing till the ingredient was dissolved. NaOH (5 M) was added to adjust the pH to 3.2 and water was added to adjust the volume to 100 mL.

Example 13: Pharmaceutical Product Suitable for Reconstitution

A first glass bottle filled with 23 g of a powder blend having the composition given in the table below was prepared.

| Ingredient | Amount |
| --- | --- |
| hemi (L)-tartrate form of rilematovir | 5.75 g |
| mannitol | 17.02 g |
| silicon dioxide | 230 mg |

A second glass bottle filled with 100 mL of a solution having the composition given in the table below was prepared.

| Ingredient | Amount |
| --- | --- |
| (L)-tartaric acid | 885.7 mg |
| HPMC 2910 | 5902 mg |
| sodium methyl paraben | 134.6 mg |
| sodium ethyl paraben | 66.69 mg |
| sucralose | 590.2 mg |
| strawberry flavor | 118.0 mg |
| simethicone | 35.41 mg |
| NaOH | to adjust pH to 3.2 |
| purified water | to adjust to volume of 100 mL |

Preparation

Water (80 mL) was transferred into a compounding vessel, simethicone was added and a high shear homogenizer was used to homogenize until a homogeneous emulsion was obtained. Then HPMC, sodium methyl paraben, sodium ethyl paraben, (L)-tartaric acid, sucralose, and strawberry flavor were added in succession, each time followed by mixing till the ingredient was dissolved. NaOH (5 M) was added to adjust the pH to 3.2 and water was added to adjust the volume to 100 mL.

Example 14: Reconstituted Liquid Aqueous Suspension of Example 12

A suspension having the composition given in the table below was prepared using pharmaceutical product from Example 12: i.e. a first bottle with a powder blend and a second bottle with a solution.

Before adding 93.8 mL of the solution: the bottle with the powder blend was swirled to loosen the powder content. After adding diluent, the bottle was inversed and tapped against the wall of the bottle to make the powder come loose from the bottom. Next, the bottle was shaken vigorously for 1 to 2 minutes, yielding a suspension with the following composition.

| Ingredient | Amount |
| --- | --- |
| hemi (L)-tartrate form of rilematovir | 2.30 g |
| mannitol | 6.81 g |
| silicon dioxide | 92 mg |
| (L)-tartaric acid | 750 mg |
| HPMC 2910 | 5000 mg |
| sodium methyl paraben | 114.0 mg |
| sodium ethyl paraben | 57 mg |
| sucralose | 500 mg |
| strawberry flavor | 100 mg |
| simethicone | 30 mg |
| NaOH | to adjust pH to 3.2 |
| purified water | |

Example 15: Reconstituted Liquid Aqueous Suspension of Example 13

A suspension having the composition given in the table below was prepared using pharmaceutical product from Example 13: i.e. a first bottle with a powder blend and a second bottle with a solution.

Before adding 84.7 mL of the solution: the bottle with the powder blend was swirled to loosen the powder content. After adding diluent, the bottle was inversed and tapped against the wall of the bottle to make the powder come loose from the bottom. Next, the bottle was shaken vigorously for 1 to 2 minutes, yielding a suspension with the following composition.

| Ingredient | Amount |
| --- | --- |
| hemi (L)-tartrate form of rilematovir | 5.75 g |
| mannitol | 17.02 g |
| silicon dioxide | 230 mg |
| (L)-tartaric acid | 750 mg |
| HPMC 2910 | 5000 mg |
| sodium methyl paraben | 114 mg |
| sodium ethyl paraben | 57 mg |
| sucralose | 500 mg |
| strawberry flavor | 100 mg |
| simethicone | 30 mg |
| NaOH | to adjust pH to 3.2 |
| purified water | |

Example 16: DSC Thermogram of Hemi (L)-Tartrate Form of Rilematovir, Form 1 and Form 3

Figure 4:
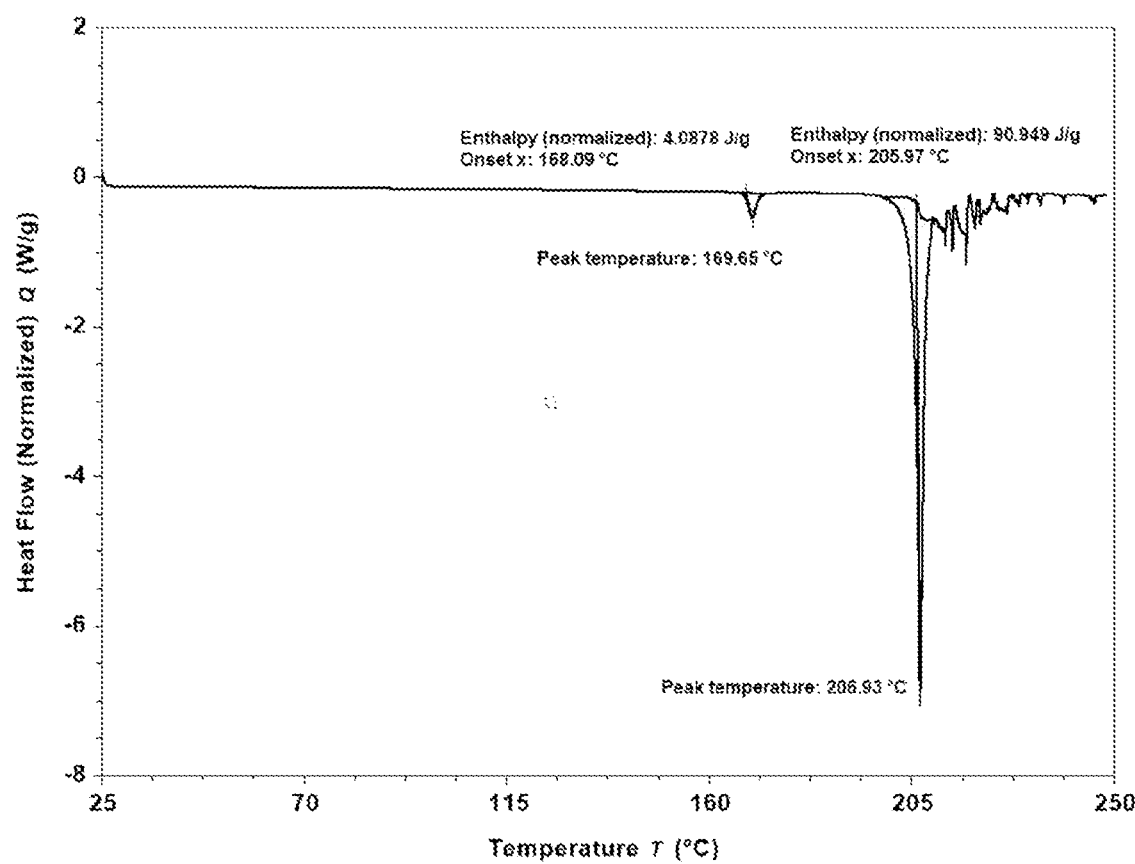
FIG. 4 DSC thermogram of hemi (L)-tartrate form of rilematovir, Form 1
Figure 5:
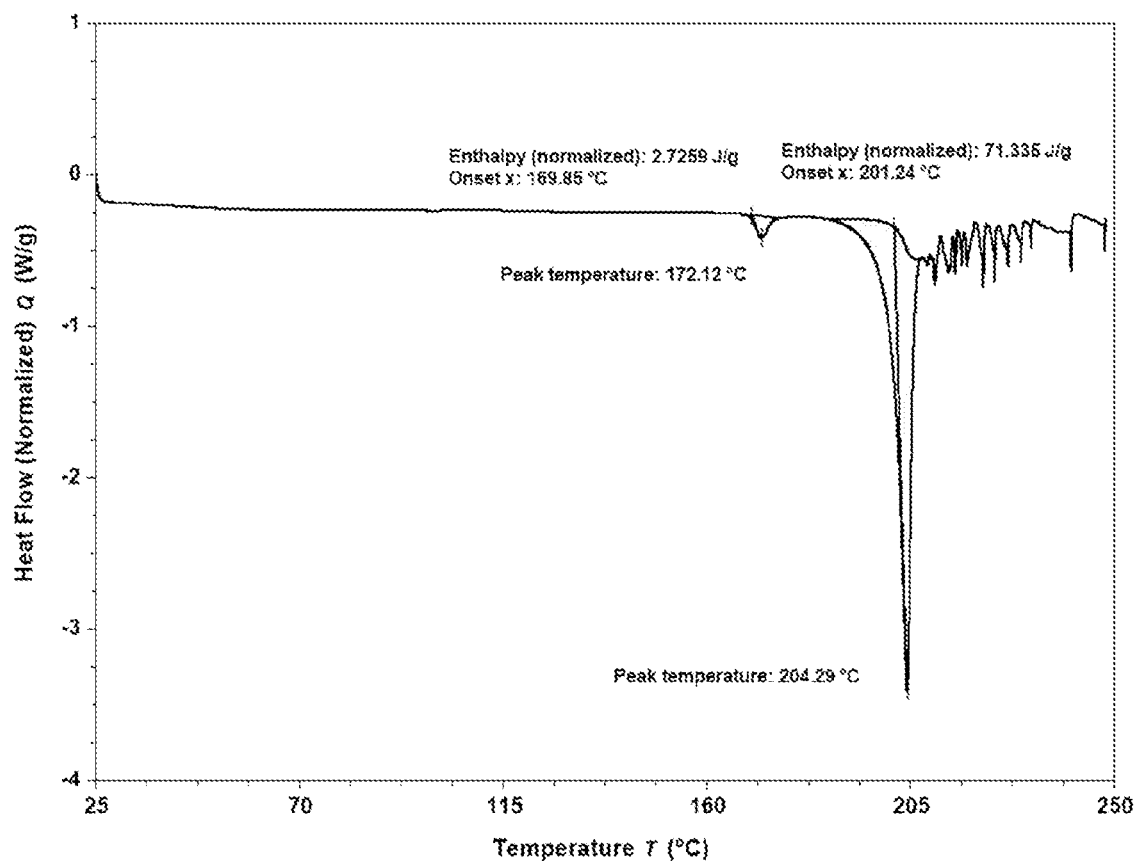
FIG. 5 DSC thermogram of hemi (L)-tartrate form of rilematovir, Form 3

DSC data were collected on a TA-Instruments Q2000 MTDSC equipped with RCS cooling unit. Typically 3 mg of each compound, in a standard aluminium TA-Instrument sample pan, was heated at 10° C./min from 25° C. to 250° C. A nitrogen purge at 50 ml/min was maintained over the sample. The DSC thermograms are represented in FIGS. 4 and 5.

Example 17: Intrinsic Dissolution Rate of Rilematovir Four Other Co-Crystal Forms of Rilematovir Intrinsic Dissolution Method Parameters:

| Apparatus | μDISS Profiler ™ |
| --- | --- |
| Stirrer speed | 100 rpm |
| Medium | 0.01N HCl-Blank FaSSIf-FaSSIF |
| Volume | 20 mL |
| Temperature | 37.0 ± 0.5° C. |
| Pathlenght fiber optic | 5 mm |
| Analytical Method for 0.01N HCl and | UV detection at 278 nm with baseline correction |

29
-continued

| Apparatus | μDISS Profiler ™ |
|---|---|
| Blank FaSSIF | at 380 nm |
| Analytical Method for FaSSIF | $2^{nd}$ derivative between the range of UV detection at 306 nm to 324 nm |

FaSSIF: Fasted State Simulated Intestinal Fluid
Blank FaSSIF: FaSSIF without presence of bile components Pellet Compression Parameters

| Apparatus: | Mini-IDR compression system |
|---|---|
| Amount of drug substance: | 5 mg of pure drug substance |
| Compression: | 40 bar for 1 minute |
| Pellet Area: | 0.0754 cm² |

TABLE 5 intrinsic dissolution rate (IDR) for rilematovir (free base) and four other co-crystal forms of rilematovir

| Test compound | Medium: 0.01N HCl IDR (μg/min/cm²) | Medium: Blank FaSSIF IDR (μg/min/cm²) | Medium: FASSIF IDR (μg/min/cm²) |
|---|---|---|---|
| free base | 8.98 | 3.06 | <1 |
| fumaric co-crystal | 4.42 | 1.39 | 1.27 |
| malonic co-crystal | 1.57 | 1.11 | 1.80 |
| hemi oxalic co-crystal | 32.77 | 1.62 | 1.18 |
| pamoic co-crystal | 1.38 | 2.79 | 19.3 |

The fumaric, malonic, hemi oxalic and pamoic crystalline co-crystal forms were obtained by suspending the free base form of rilematovir in a solvent, heating to reflux temperature till a clear solution is obtained, followed by cooling to room temperature and isolating the suspended crystalline material by filtration. Melting points were measured by DSC. In the table below, the crystallisation solvent and melting point are listed for the four co-crystal forms.

| Co-crystal form | Solvent | Melting point (DSC) |
|---|---|---|
| fumaric co-crystal | ethanol/water (90/10) | 224° C. |
| malonic co-crystal | acetone | 164° C. |
| hemi oxalic co-crystal | THF/water (95/5) | 226° C. |
| pamoic co-crystal | ethyl acetate | 236° C. |

30

The invention claimed is:
1. A compound of formula

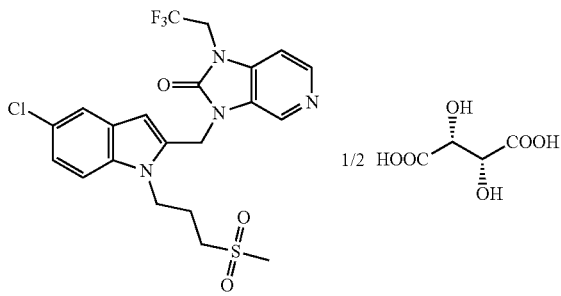 [SMILES: CS(=O)(=O)CCCn1c(Cn2c(=O)n(CC(F)(F)F)c3ccncc32)cc2cc(Cl)ccc21 ; O=C(O)[C@H](O)[C@@H](O)C(=O)O]

that is a hemi (L)-tartrate form of rilematovir,
wherein the compound is in crystalline form and
wherein the crystalline form is selected from Form 1, Form 2, Form 3, or mixtures thereof,
where:
Form 1 is characterized by an X-ray powder diffraction pattern comprising peaks at 12.4, 15.8, 16.2, 18.0, 20.2, 22.7, and 26.7 degrees two theta ±0.2 degrees two theta when measured using Cu Kα radiation;
Form 2 is characterized by an X-ray powder diffraction pattern comprising peaks at 14.4, 14.7, 16.4, 17.1, 19.0, 19.4, and 20.7 degrees two theta ±0.2 degrees two theta when measured using Cu Kα radiation; and
Form 3 is characterized by an X-ray powder diffraction pattern comprising peaks at 8.2, 12.2, 15.3, 15.5, 16.2, 16.5, and 18.8 degrees two theta ±0.2 degrees two theta when measured using Cu Kα radiation.
2. The compound of claim 1, wherein the crystalline form is Form 1.
3. The compound of claim 1, wherein the crystalline form is Form 2.
4. The compound of claim 1, wherein the crystalline form is Form 3.
5. A pharmaceutical product comprising a first pharmaceutical composition and a second pharmaceutical composition, wherein the first pharmaceutical composition comprises
a) a crystalline hemi (L)-tartrate form of rilematovir in a concentration from 20% (w/w) to 100% (w/w), wherein the form is selected from Form 1, Form 2, and Form 3, and mixtures thereof, and
b) a bulking agent to make up to 100% (w/w); and
the second pharmaceutical composition comprises
a) (L)-tartaric acid,
b) a suspending agent,
c) optional excipients, optionally wherein the optional excipients are selected from preservatives, sweeteners, anti-foaming agents, flavouring agents, pH adjusting agents, and wetting agents, and combinations thereof, and
d) water,
wherein the pH of the second pharmaceutical composition ranges from 2.8 to 3.6, where:
Form 1 is characterized by an X-ray powder diffraction pattern comprising peaks at 12.4, 15.8, 16.2, 18.0, 20.2, 22.7, and 26.7 degrees two theta ±0.2 degrees two theta when measured using Cu Kα radiation, optionally wherein the X-ray powder diffraction pattern comprises peaks at 7.9, 18.5, 19.3, 21.9, 22.3, 24.2, and 27.9 degrees two theta ±0.2 degrees two theta when measured using Cu Kα radiation;

Form 2 is characterized by an X-ray powder diffraction pattern comprising peaks at 14.4, 14.7, 16.4, 17.1, 19.0, 19.4, and 20.7 degrees two theta ±0.2 degrees two theta when measured using Cu Kα radiation, optionally wherein the X-ray powder diffraction pattern comprises peaks at 14.1, 18.4, 21.7, 22.6, 23.5, 27.3, and 27.8 degrees two theta ±0.2 degrees two theta when measured using Cu Kα radiation; and Form 3 is characterized by an X-ray powder diffraction pattern comprising peaks at 8.2, 12.2, 15.3, 15.5, 16.2, 16.5, and 18.8 degrees two theta ±0.2 degrees two theta when measured using Cu Kα radiation, optionally wherein the X-ray powder diffraction pattern comprises peaks at 12.4, 17.0, 20.6, 21.8, 23.2, 24.6, and 27.4 degrees two theta ±0.2 degrees two theta when measured using Cu Kα radiation.

6. The pharmaceutical product of claim 5, wherein, in the second pharmaceutical composition, the suspending agent is in a concentration ranging from 10 mg/mL to 100 mg/mL, wherein the suspending agent is selected from the group consisting of colloidal anhydrous silica, methylcellulose, microcrystalline cellulose, sodium carboxymethylcellulose, carrageenan, xanthan gum, and hydroxypropylmethylcellulose.

7. The pharmaceutical product of claim 5, wherein the bulking agent is present and is selected from the group consisting of powdered cellulose, magnesium stearate, sodium bicarbonate, sodium silicate, silicon dioxide, fumed silica, bentonite, stearic acid, polydimethylsiloxane, and mannitol, or a combination thereof, optionally wherein the bulking agent is a combination of mannitol and silicon dioxide.

8. A kit comprising the pharmaceutical product of claim 5 and instructions for reconstituting the first pharmaceutical composition and the second pharmaceutical composition into a liquid aqueous suspension formulation; and optionally a container for reconstituting.

9. A process for preparing the crystalline hemi (L)-tartrate form of rilematovir that is Form 1 of claim 2, comprising crystallizing a hemi (L)-tartrate form of rilematovir from a solvent selected from the group consisting of acetone, acetonitrile, 2-propanol, methyl ethyl ketone, and THF, and mixtures thereof.

10. The process of claim 9, wherein the crystalline hemi (L)-tartrate form of rilematovir is further characterized by the X-ray powder diffraction pattern comprising peaks at 7.9, 18.5, 19.3, 21.9, 22.3, 24.2, and 27.9 degrees two theta ±0.2 degrees two theta when measured using Cu Kα radiation.

11. The compound of claim 2, wherein Form 1 is further characterized by the X-ray powder diffraction pattern comprising peaks at 7.9, 18.5, 19.3, 21.9, 22.3, 24.2, and 27.9 degrees two theta ±0.2 degrees two theta when measured using Cu Kα radiation.

12. The compound of claim 3, wherein Form 2 is further characterized by the X-ray powder diffraction pattern comprising peaks at 14.1, 18.4, 21.7, 22.6, 23.5, 27.3, and 27.8 degrees two theta ±0.2 degrees two theta when measured using Cu Kα radiation.

13. The compound of claim 4, wherein Form 3 is further characterized by the X-ray powder diffraction pattern comprising peaks at 12.4, 17.0, 20.6, 21.8, 23.2, 24.6, and 27.4 degrees two theta ±0.2 degrees two theta when measured using Cu Kα radiation.

14. The pharmaceutical product of claim 5, wherein the crystalline form is Form 1.

15. The pharmaceutical product of claim 5, wherein the crystalline form is Form 2.

16. The pharmaceutical product of claim 5, wherein the crystalline form is Form 3.

17. The pharmaceutical product of claim 14, wherein Form 1 is further characterized by the X-ray powder diffraction pattern comprising peaks at 7.9, 18.5, 19.3, 21.9, 22.3, 24.2, and 27.9 degrees two theta ±0.2 degrees two theta when measured using Cu Kα radiation.

18. The pharmaceutical product of claim 15, wherein Form 2 is further characterized by the X-ray powder diffraction pattern comprising peaks at 14.1, 18.4, 21.7, 22.6, 23.5, 27.3, and 27.8 degrees two theta ±0.2 degrees two theta when measured using Cu Kα radiation.

19. The pharmaceutical product of claim 16, wherein Form 3 is further characterized by the X-ray powder diffraction pattern comprising peaks at 12.4, 17.0, 20.6, 21.8, 23.2, 24.6, and 27.4 degrees two theta ±0.2 degrees two theta when measured using Cu Kα radiation.

* * * * *